(12) United States Patent
Danuser et al.

(10) Patent No.: US 8,237,786 B2
(45) Date of Patent: Aug. 7, 2012

(54) SYSTEM AND METHOD FOR DENSE-STOCHASTIC-SAMPLING IMAGING

(75) Inventors: Gaudenz Danuser, Cambridge, MA (US); Paul C. Goodwin, Shoreline, WA (US)

(73) Assignee: Applied Precision, Inc., Issaquah, WA (US)

( * ) Notice: Subject to any disclaimer, the term of this patent is extended or adjusted under 35 U.S.C. 154(b) by 268 days.

(21) Appl. No.: 12/751,816

(22) Filed: Mar. 31, 2010

(65) Prior Publication Data
US 2011/0149097 A1    Jun. 23, 2011

Related U.S. Application Data

(60) Provisional application No. 61/289,916, filed on Dec. 23, 2009.

(51) Int. Cl.
H04N 9/47       (2006.01)
H04N 13/04      (2006.01)
(52) U.S. Cl. ......................................................... 348/79
(58) Field of Classification Search ...................... 348/79
See application file for complete search history.

(56) References Cited

U.S. PATENT DOCUMENTS

| | | | | |
|---|---|---|---|---|
| 5,622,170 A * | 4/1997 | Schulz | ........................ | 600/424 |
| 2002/0131165 A1* | 9/2002 | Takahama | ..................... | 359/381 |
| 2003/0169423 A1* | 9/2003 | Finarov et al. | ................ | 356/401 |
| 2006/0127369 A1 | 6/2006 | Christensen et al. | | |
| 2006/0149481 A1 | 7/2006 | Stein et al. | | |
| 2008/0137937 A1 | 6/2008 | Athelogou et al. | | |
| 2009/0155780 A1 | 6/2009 | Xiao et al. | | |
| 2009/0242798 A1 | 10/2009 | Bewersdorf et al. | | |

OTHER PUBLICATIONS

International Search Report Issued on Corresponding PCT Application US2010/059447 Dated Sep. 20, 2011.

* cited by examiner

*Primary Examiner* — David Czekaj
*Assistant Examiner* — Anner Holder

(57) ABSTRACT

Embodiments of the present invention are directed to imaging technologies, and, in particular, to an imaging system that detects relatively weak signals, over time, and that uses the detected signals to determine the positions of signal emitters. Particular embodiments of the present invention are directed to methods and systems for imaging fluorophore-labeled samples in order to produce images of the sample at resolutions significantly greater than the diffraction-limited resolution associated with optical microscopy. Embodiments of the present invention employ overlapping-emitter-image disambiguation to allow data to be collected from densely arranged emitters, which significantly decreases the data-collection time for producing intermediate images as well as the number of intermediate images needed to computationally construct high-resolution final images. Additional embodiments of the present invention employ hierarchical image-processing techniques to further resolve and interpret disambiguated images.

20 Claims, 38 Drawing Sheets

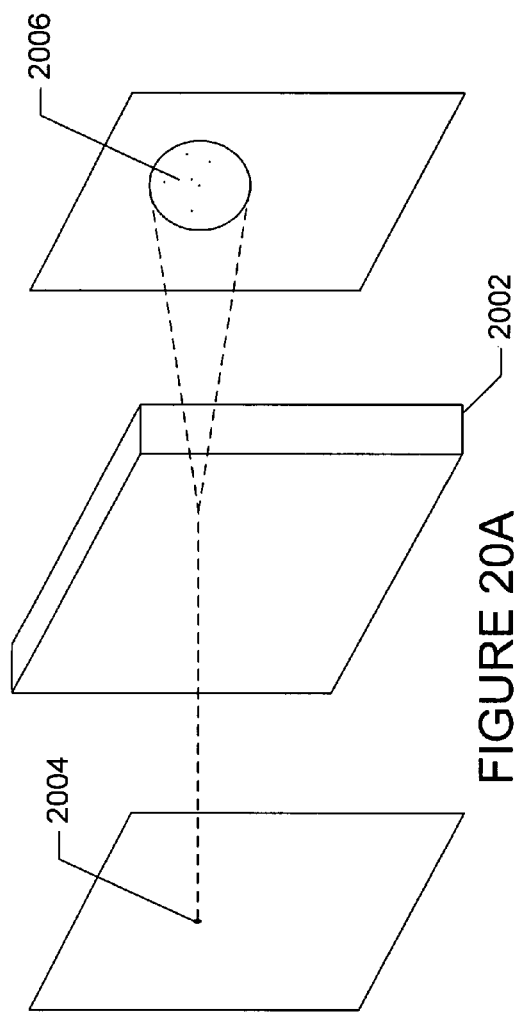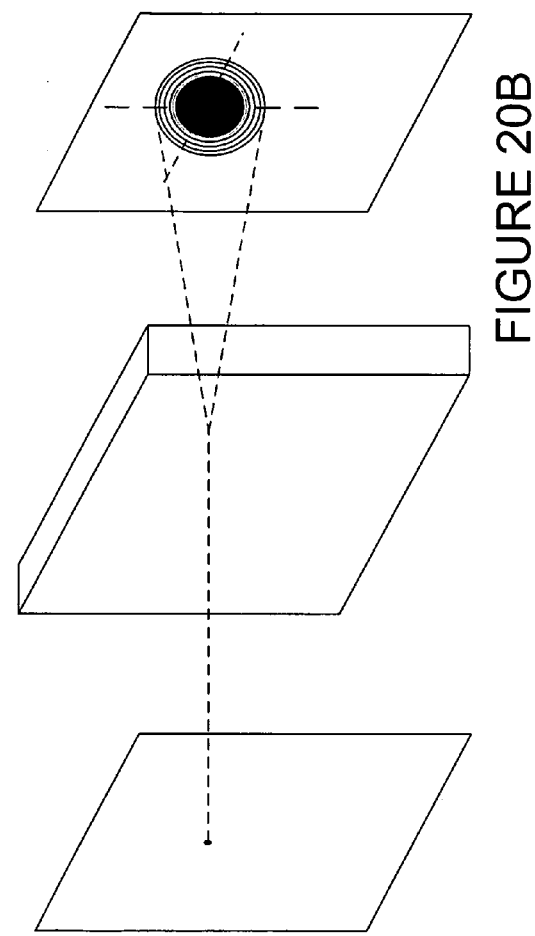

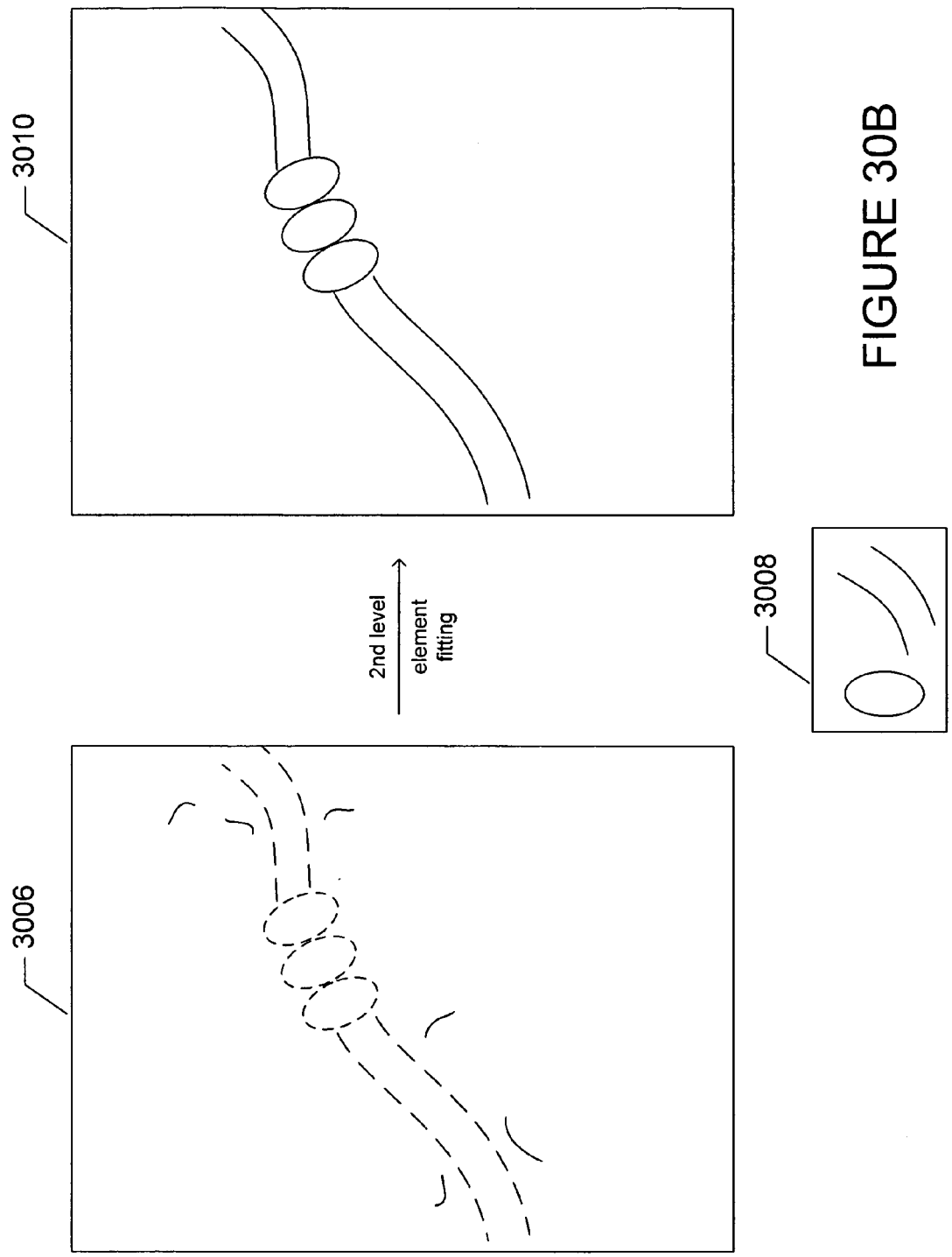

SYSTEM AND METHOD FOR DENSE-STOCHASTIC-SAMPLING IMAGING

CROSS-REFERENCE TO RELATED APPLICATION

This application claims the benefit of Provisional Application No. 61/289,916; filed Dec. 23, 2009.

TECHNICAL FIELD

The present invention is related to imaging technologies, and, in particular, to an imaging system that detects relatively weak signals, over time, and that uses the detected signals to determine the positions of signal emitters.

BACKGROUND

Many different types of imaging systems are employed in modern scientific research to acquire images of small or distant objects, including extremely high-resolution electron microscopes, extremely high-resolution scanning tunneling ("STM") and atomic-force ("AFM") imaging instruments, and many different types of optical microscopes, telescopes, and image-generating sensors. As with most types of imaging devices, instruments, and techniques, there are many different trade-offs and balances associated with different types of microscopy. For example, transmission electron microscopy is carried out on fixed and thinly-sectioned samples, and is therefore constrained for use on essentially two-dimensional, non-living samples. Scanning-tunneling and atomic-force microscopy are non-optical techniques for obtaining high-resolution images of the surfaces of materials, but cannot be used to obtain information about the nanoscale or microscale contents of volumes of samples below surfaces. All types of microscopy are constrained, in one way or another, by resolution limitations, but optical microscopy is associated with the perhaps best-known resolution limitation referred to as the "diffraction limit," which limits traditional visible-light optical microscopy to a resolution limit of about 200 nm.

During the past 20 years, various super-resolution techniques have been developed to allow imaging of fluorophore-labeled samples, most often biological samples, by optical fluorescence-microscopy instruments at resolutions significantly below the diffraction-limited resolution for traditional optical microscopy. These techniques are based on collecting fluorescent light emitted from fluorophore-labeled samples over time. Providing that the emitting fluorophores are separated from one another by distances greater than approximately 200 nm, or, in other words, provided that the positions of the fluorophores in the sample would be resolvable by traditional optical microscopy, the positions of the fluorophores in a sample can be determined, in certain cases, to a resolution of below 10 nm. However, because the fluorescent-emission signal can be interpreted only when the emitting fluorophores are sparsely arranged within the sample, a generally large number of intermediate images need to be produced from different sets of sparsely arranged fluorophores in order to construct a super-resolution, final image of a fluorophore-labeled object. Thus, super-resolution images are obtained at the expense of the time needed to accumulate a relatively weak signal to produce a larger number of intermediate images. The time needed for super-resolution imaging does not favor imaging of live cells, which tend to move and change shape over the periods of time needed to collect the relatively weak signal from which super-resolution images are constructed. The long time periods needed to collect the relatively weak signal may also result in exposure of living cells to deleterious or fatal levels of electromagnetic radiation, including ultraviolet light. The time needed to acquire sufficient data for super-resolution imaging may also represent a significant experimental constraint, regardless of the type of sample that is imaged. For all of these reasons, those who design and develop, manufacture, and use super-resolution imaging methodologies and instrumentation continue to seek new and improved methodologies and instrumentation that are associated with fewer time and sample-preparation constraints than currently available super-resolution methodologies and instrumentation.

SUMMARY

Embodiments of the present invention are directed to imaging technologies, and, in particular, to an imaging system that detects relatively weak signals, over time, and that uses the detected signals to determine the positions of signal emitters. Particular embodiments of the present invention are directed to methods and systems for imaging fluorophore-labeled samples in order to produce images of the sample at resolutions significantly greater than the diffraction-limited resolution associated with optical microscopy. Embodiments of the present invention employ overlapping-emitter-image disambiguation to allow data to be collected from densely arranged emitters, which significantly decreases the data-collection time for producing intermediate images as well as the number of intermediate images needed to computationally construct high-resolution final images. Additional embodiments of the present invention employ hierarchical image-processing techniques to further refine and interpret disambiguated images.

BRIEF DESCRIPTION OF THE DRAWINGS

FIGS. 20A-B illustrate a basis for super-resolution microscopy.

FIGS. 30A-D illustrate the processes carried out in steps 2313 and 2314 of FIG. 23, according to one embodiment of the present invention.

DETAILED DESCRIPTION OF THE INVENTION

Embodiments of the present invention are directed to imaging technologies, and, in particular, to an imaging system that detects relatively weak signals, over time, and that uses the detected signals to determine the positions of signal emitters. In the following discussion, embodiments of the present invention directed to methods and instrumentation for imaging samples, particularly biological samples, at resolutions greater than the so-called diffraction-limited resolution of traditional optical microscopes serve as the context for describing the present invention. However, alternative embodiments of the present invention are directed to many other imaging applications. Embodiments of the present invention employ various computational image-processing methodologies, discussed in great detail, below, for disambiguation of overlapping emitter images, for hierarchically fitting of geometrical elements to images in order to further refine the raw images, and for interpreting images.

Figure 1B:
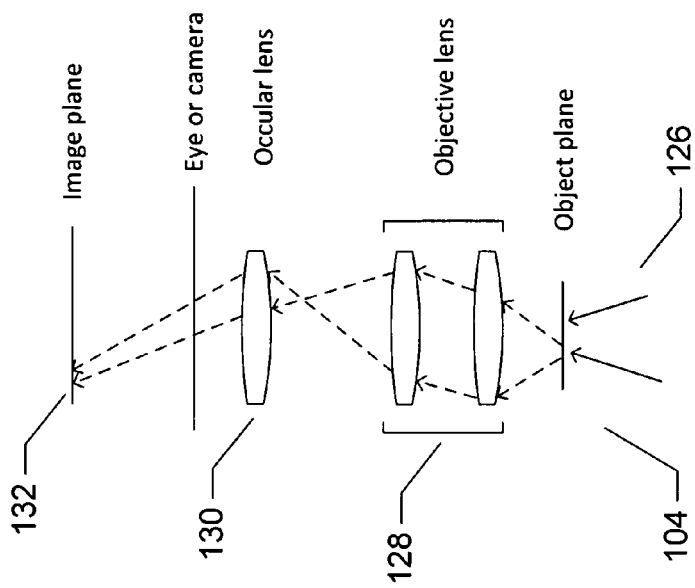
FIGS. 1A-B illustrate a typical optical microscope.
Figure 1A:
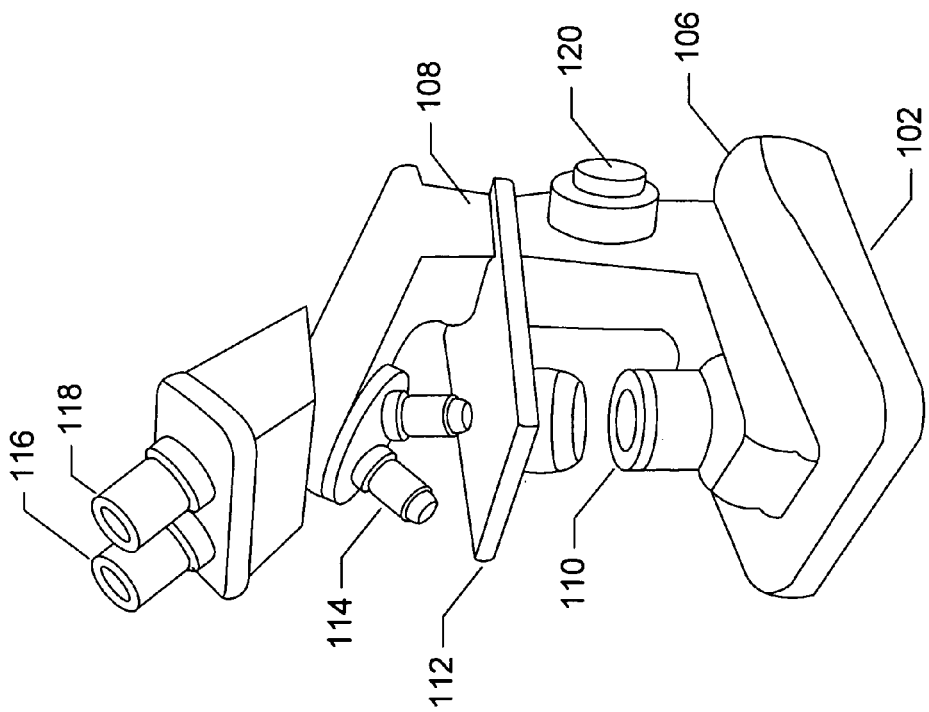

FIGS. 1A-B illustrate a typical optical microscope. FIG. 1A shows the external appearance of an optical microscope 102 and FIG. 1B illustrates the optical path 104 within a typical optical microscope. The optical microscope includes a base 106 and vertical support 108 that together support a light source 110, sample stage 112, numerous, rotatably-mounted objective lenses 114, and one or more ocular lenses within each of two eyepieces 116 and 118. A sample is generally placed on a glass slide, which is, in turn, mounted to the upper surface of the sample stage 112 for viewing. The distance between the objective lens and sample can be adjusted by a focus knob 120 in order to optically focus particular horizontal planes within the sample. Within the microscope, the optical light path comprises light emitted by the light source 126 that passes through the sample, one or more objective lenses 128, one or more tube lenses, one or more ocular lenses 130, and that is focused by the system of lenses onto an image plane 132 within a human eye, camera, charge-coupled-device detector ("CCD"), or other type of spatial-intensity detector.

Figure 2B:
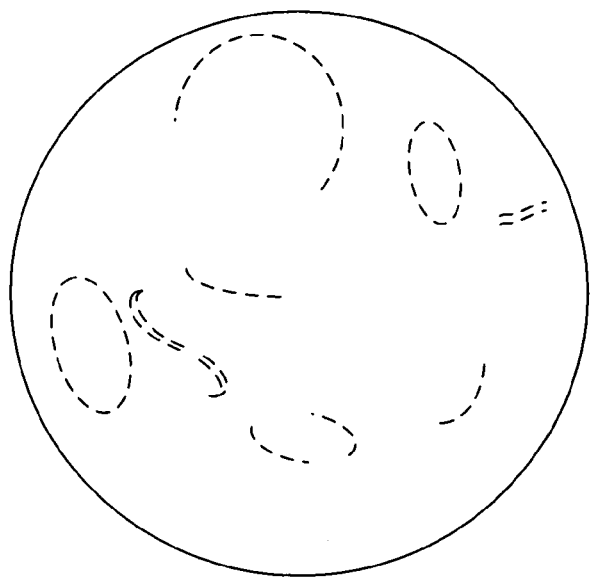
FIGS. 2A-B illustrate an imaging problem associated with visible-light optical-microscopy imaging of biological samples.
Figure 2A:
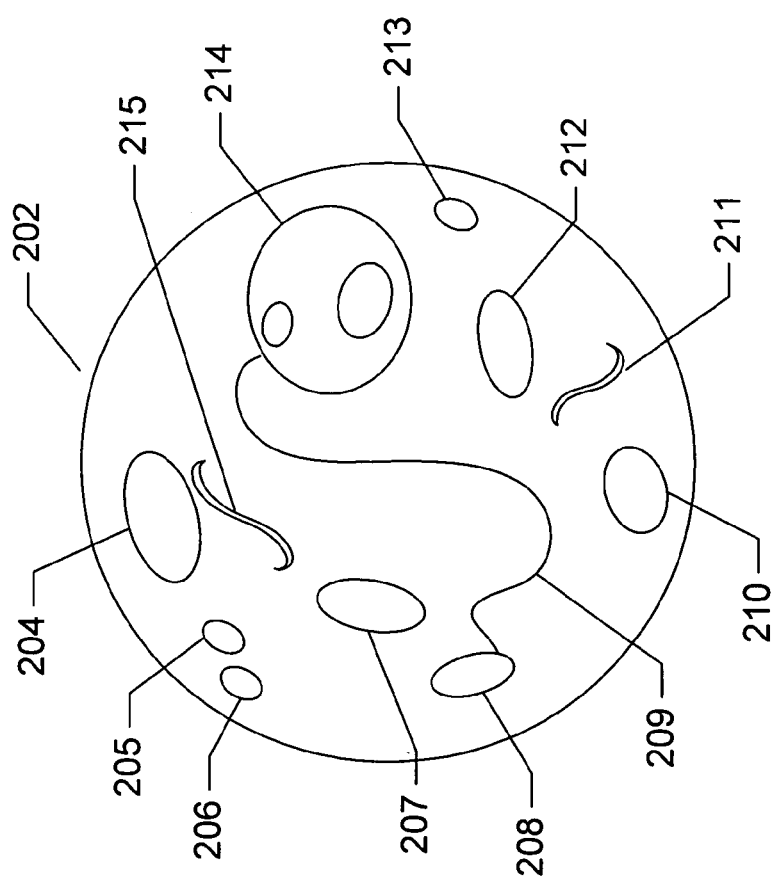

FIGS. 2A-B illustrate an imaging problem associated with visible-light optical-microscopy imaging of biological samples. FIG. 2A shows an idealized, abstract, disk-shaped portion of an object plane within a biological sample 202. The portion of an object plane includes various different types of microscale and sub-microscale cellular structures 204-215. These structures may include various internal organelles, membranes within a cell, and other such cellular components. Although the different cellular components may have different functions and chemical compositions, they generally have similar optical characteristics, and thus, as shown in FIG. 2B, when viewed using traditional optical microscopy, appear relatively undifferentiated from one another and are often distinguishable from the background. In order to improve the contrast between different types of cellular components, microscopists often stain biological samples with various chemical stains that are differentially absorbed by different components. However, many different types of components remain indistinguishable from one another even after staining, and, more importantly, stains are generally cytotoxic and the staining and fixing process generally involves killing the cells of the biological tissue.

Figure 3A:
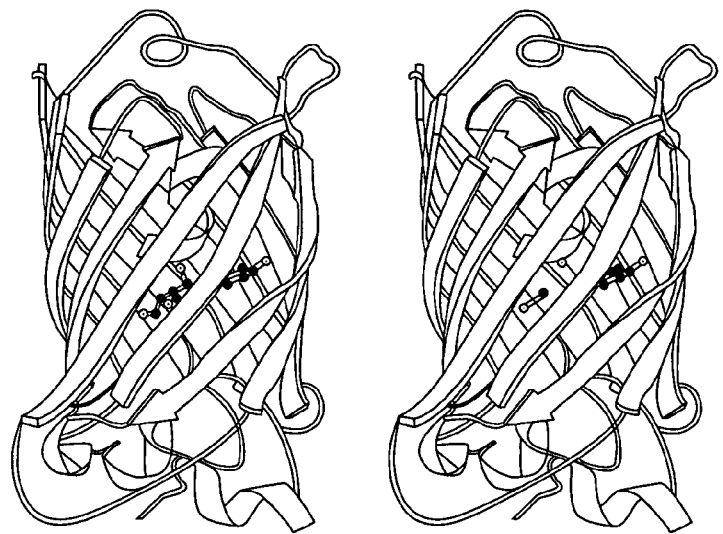
FIGS. 3A-B illustrate characteristics of the green fluorescent protein ("GFP").
Figure 3B:
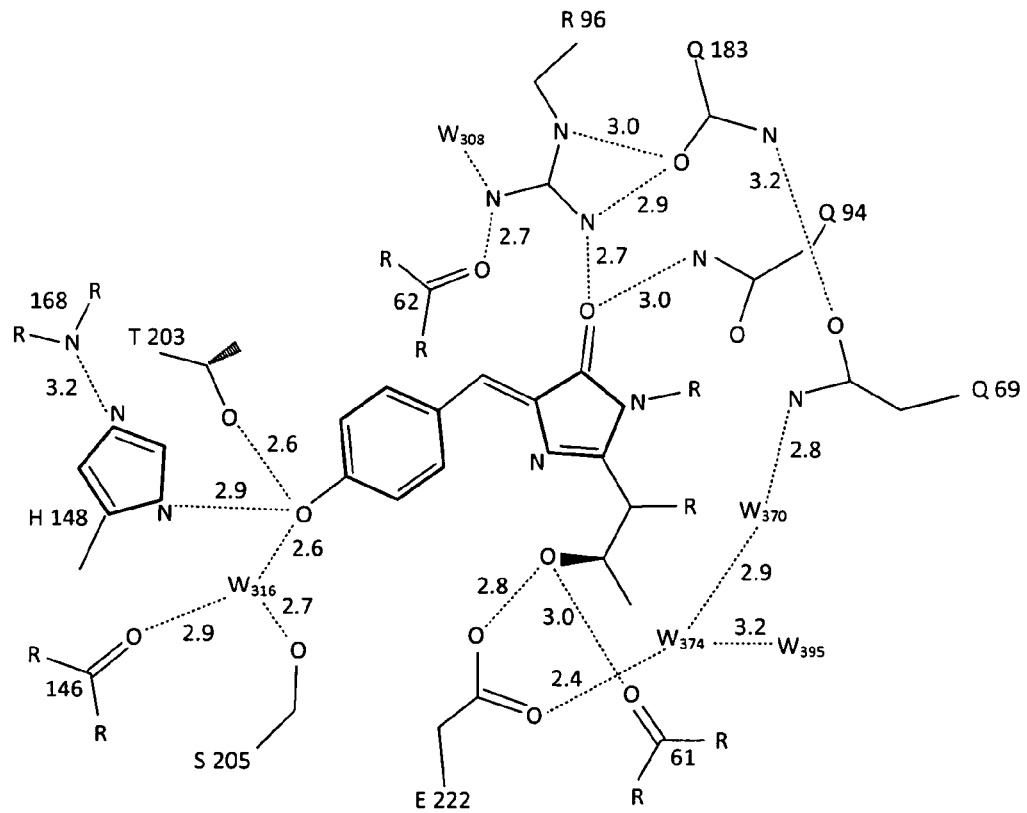

More recently, fluorescence microscopy methods and instrumentation have been developed to address certain of the imaging problems associated with traditional optical microscopy, including the problem discussed above with reference to FIGS. 2A-B. Fluorescence microscopy has been significantly advanced by the discovery and exploitation of the green fluorescent protein ("GFP"), a 238-amino acid (26.9 kDa) protein originally isolated from the jellyfish *Aequorea victoria*, and related biological and chemical fluorophores. FIGS. 3A-B illustrate characteristics of the green fluorescent protein ("GFP"). The stereo image in FIG. 3A shows the beta-barrel three-dimensional structure of GFP. In the interior of the beta barrel, the side chains of a number of amino-acid-monomer subunits of GFP combine to produce a fluorophore, the chemical structure of which is shown in FIG. 3B. The fluorophore is shown, in FIG. 3A, as a ball-and-stick model within the GFP beta barrel represented by oriented ribbons.

Figure 4:
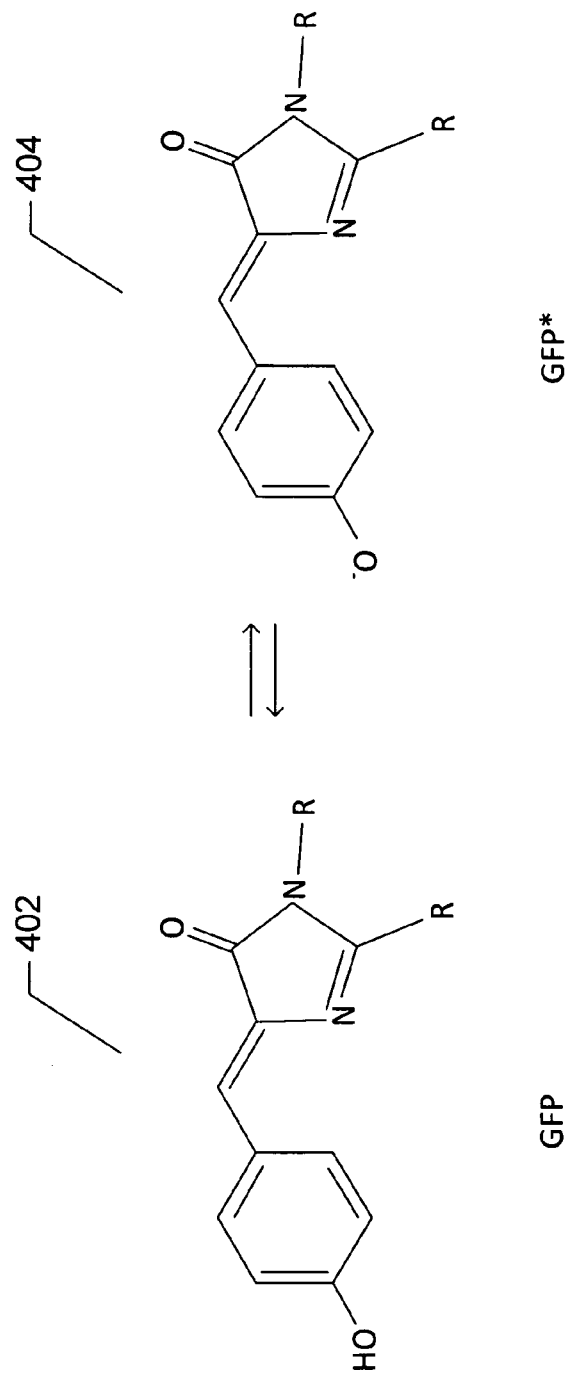
FIG. 4 shows interconversion of the GFP fluorophore between a neutral form and an anionic form.
Figure 5A:
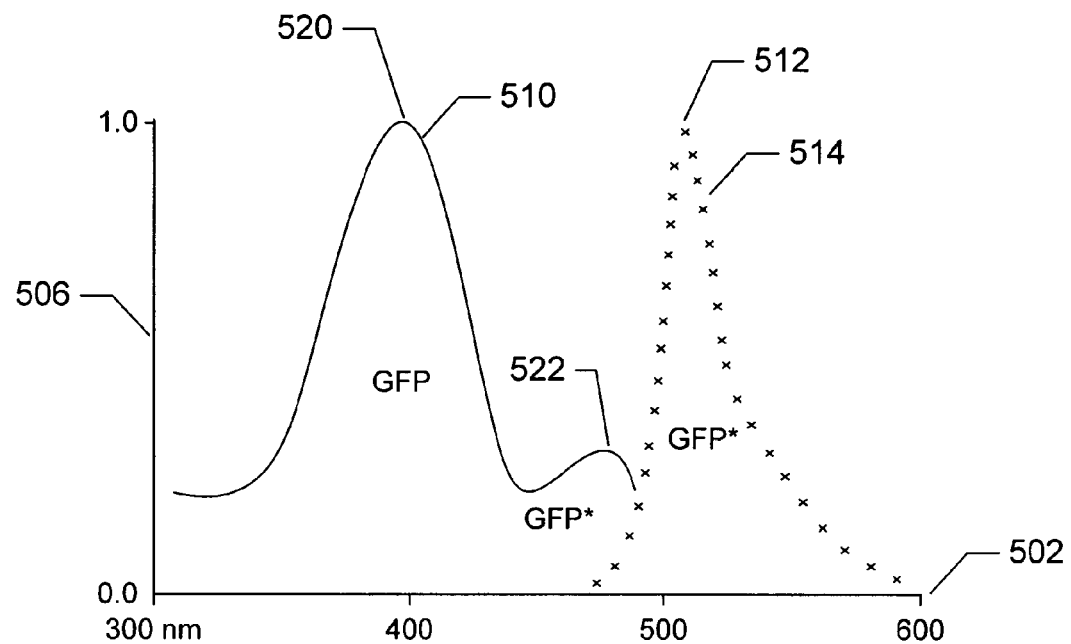
FIGS. 5A-B show absorption and emission curves for GFP and GFP*.
Figure 5B:
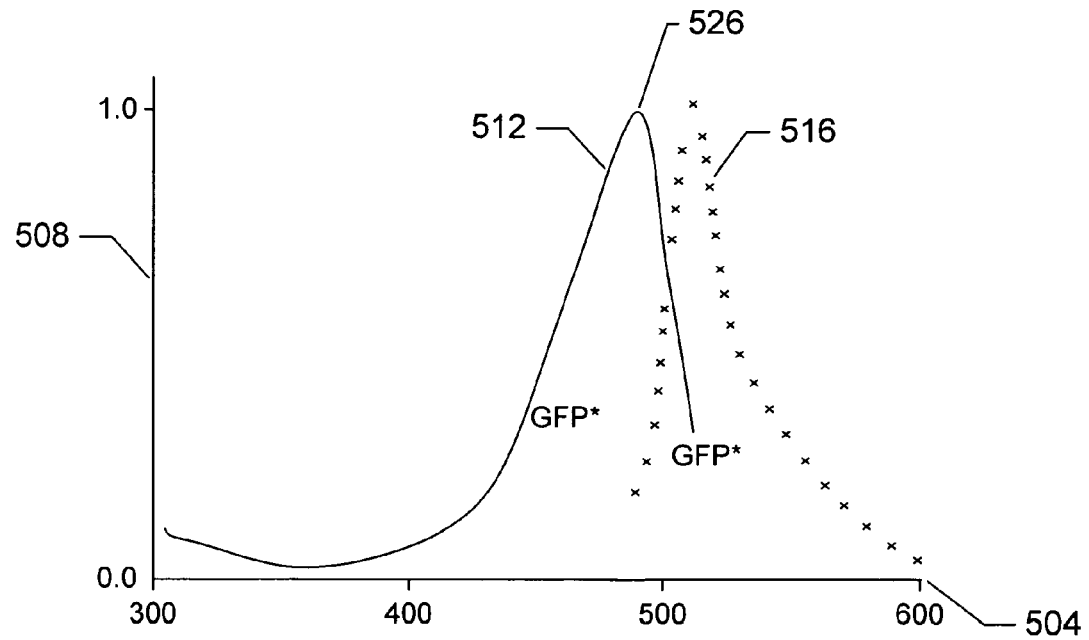

FIG. 4 shows interconversion of the GFP fluorophore between a neutral form and an anionic form. When the fluorophore within GFP is in the neutral form, the GFP is not activated, and is designated, in the following discussion, as "GFP." When the fluorophore within GFP is in the anionic form 404, the GFP is activated, and is designated "GFP*." FIGS. 5A-B show absorption and emission curves for GFP and GFP*. In both FIG. 5A and FIG. 5B, the absorption and emission curves are plotted with respect to the wavelength of absorbed or emitted light on the horizontal axes 502 and 504, with the vertical axes 506 and 508 representing relative absorptivity and relative emissivity. The absorptivity curves in FIGS. 5A-B are solid curves, 510 and 512, and the emissivity curves are broken curves, 514 and 516. FIG. 5A shows the relative absorptivity and relative emissivity for an equilibrium mixture that is predominantly GFP but that contains a relatively small amount of GFP*, such equilibrium mixtures representing the state of a GFP solution prior to illumination. The absorptivity curve is bimodal, with a large peak 520 at 395 nm and a lower peak 522 at 475 nm. The bimodal absorption peak is thought to correspond to the equilibrium mixture of GFP and GFP*. Absorption of light by GFP, with maximal absorptivity at 395 nm, converts GFP to GFP*, which emits fluorescent light with maximal emissivity at 508 nm, corresponding to the peak 522 of the emission curve. GFP*, present in smaller amounts in an equilibrium mixture, maximally absorbs light of wavelength 475 nm and emits fluorescent light with maximal emissivity at 503 nm. When GFP is strongly illuminated by 395 nm light over a period of time, most of the GFP is converted to GFP*. Subsequently, the absorptivity profile of the solution shifts to that shown in FIG. 5B, with a single dominant absorption peak 526 at 475 nm, corresponding to the wavelength of maximum absorption by GFP*. Thus, there are essentially two different states of GFP. The unactivated state, GFP, maximally absorbs light at 395 nm and maximally emits fluorescent light at 508 nm, while activated GFP, GFP*, maximally absorbs light of wavelength 475 nm and maximally'emits fluorescent light of wavelength 510 nm.

The gene for GFP can be spliced into genes that encode particular protein components of an organism in order to label the proteins with the GFP fluorophore. By using standard molecular-biology techniques, scientists can precisely fluorescently label individual proteins and individual-protein-containing cellular components and structures. Importantly, the GFP fluorophore label can be introduced into living cells, without killing the cells or perturbing normal cellular function. Thus, fluorophore labeling of biological tissues and fluorescence microscopy provides a method and system for addressing the imaging problem discussed with reference to FIGS. 2A-B and problems associated with chemical stains and other techniques used to increase the contrast within biological samples.

Figure 6A:
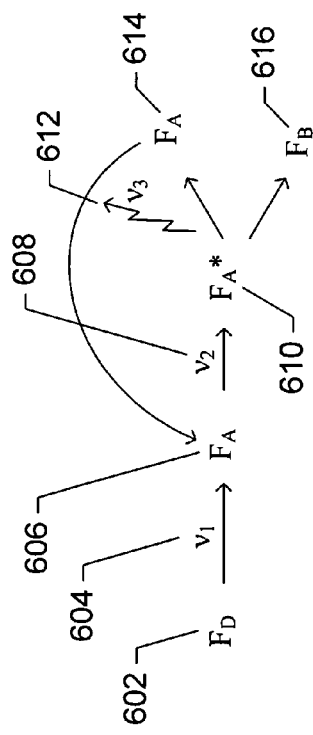
FIGS. 6A-C illustrate various types of absorption and emission characteristics observed for the various different protein and chemical fluorophores used in fluorescence microscopy.
Figure 6B:
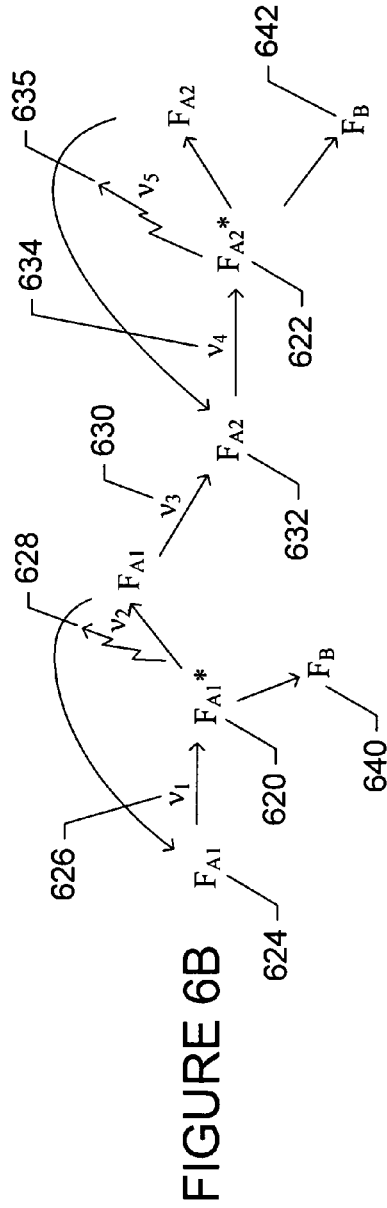
Figure 6C:
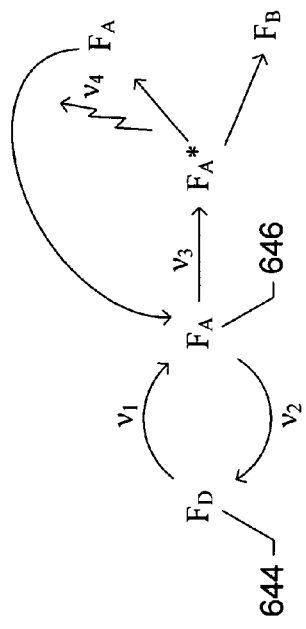

Since the discovery of GFP, a large number of GFP variants have been developed, with different absorption and emission characteristics, and other fluorescent proteins and chemical fluorophores have been discovered and/or exploited for use in fluorescence microscopy. FIGS. 6A-C illustrate various types of absorption and emission characteristics observed for the various different protein and chemical fluorophores used in fluorescence microscopy. In FIGS. 6A-C, a fluorophore is represented by the symbol "F." A non-fluorescing form of the fluorophore is designated "$F_D$." A bleached, non-fluorescing form of the fluorophore is designated as "$F_B$." Different fluorescing forms of a fluorophore that can be excited to emit fluorescent light are designated "$F_A$," "$F_{A1}$," and "$F_{A2}$." Stimulated activated fluorophores are designated by the superscript symbol "*." The different non-fluorescing and activated forms of a fluorophore may represent structurally different chemical forms of the fluorophore, different chemical environments of the fluorophore, or other relatively stable differences that effect light absorption and emission by the fluorophore. An electron of an excited form of a fluorophore has absorbed light energy and has been promoted to an excited state, from which it subsequently relaxes by emitting fluorescent light.

FIG. 6A shows a first type of fluorophore, used in fluorescence microscopy, which initially occurs in a non-fluorescing form 602. Upon illumination by light of a first frequency, $v_1$ 604, the non-fluorescing isomer is converted into an activated, fluorescing form 606. The fluorescing form 606 is excited, by absorption of light of a second frequency, $v_2$ 608, to produce an excited form of the fluorophore 610, which subsequently emits fluorescent light 612 and returns to the non-excited, activated form of the fluorophore 614. The fluorophore can undergo hundreds, thousands, or more of excitation/emission cycles, but, under continuous illumination by light of the second frequency, ultimately transforms to a bleached form 616 which can neither be activated nor excited to fluoresce. FIG. 6B shows a second type of fluorophore which features two different excited states $F_{A1}$* 620 and $F_{A2}$* 622. A first form $F_{A1}$ 624 is excited, by absorption of light of a first frequency 626, to the excited form $F_{A1}$* 620, from which light of a second frequency is emitted by fluorescence emission 628 as the excited fluorophore relaxes to the $F_{A1}$ state. Illumination of the fluorophore by light of a third frequency 630 converts the fluorophore to a second state $F_{A2}$ 632, which can be excited, by illumination with light of a fourth frequency 634, to a second excited state 622 that fluorescently emits light of a fifth frequency 635. Either of the two fluorescing forms can be bleached, by continuous illumination, to the $F_B$ state 640 and 642. FIG. 6C shows a third type of fluorophore that can be reversibly interconverted between the $F_D$ and $F_A$ states 644 and 646. The $F_A$ form can be excited to fluorescently emit light in similar fashion to excitation of the fluorophore described with reference to FIG. 6A.

Figure 7:
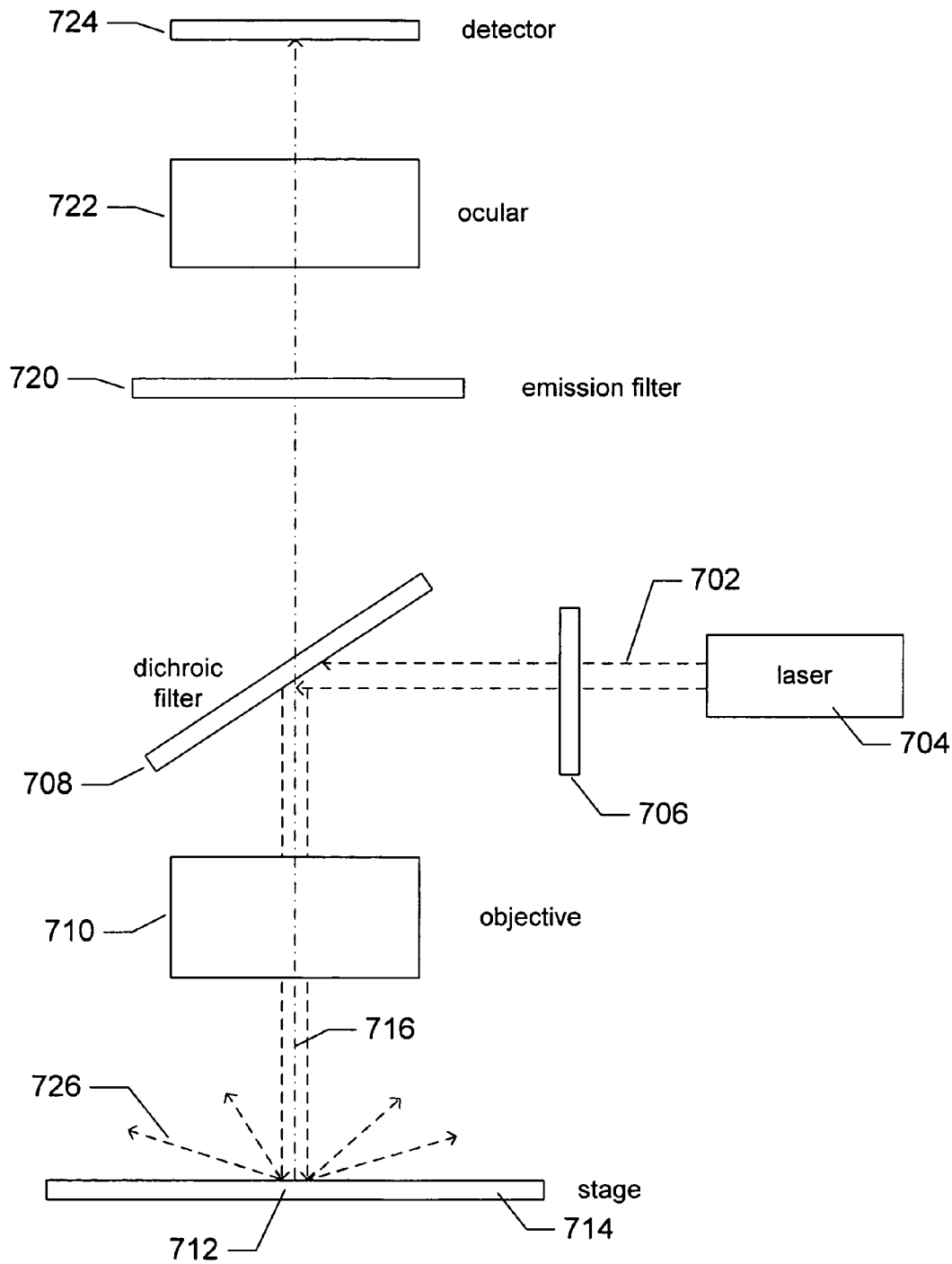
FIG. 7 illustrates the optical path within a fluorescence microscope.

FIG. 7 illustrates the optical path within a fluorescence microscope. There are many different types of fluorescence microscopes and corresponding optical paths. FIG. 7 is not intended to describe the optical paths within all the different, well-known variations of fluorescence microscopes, but to instead illustrate the general principals of fluorescence microscopy. Fluorescence-excitation light 702 is emitted from a light source, such as a laser 704, and passes through an excitation-light filter 706. The excitation light is reflected from a diagonal, dichroic mirror 708 through the objective lens or lenses 710 onto a sample 712 mounted to the stage 714. The excitation light excites fluorophores within the sample to emit fluorescent light, as discussed above. The emitted fluorescent light, shown in FIG. 7 by a broken line of dashes and asterisks 716, passes through the objective lens or lenses 710, is transmitted through the dichroic mirror 708, passes through the emission filter 720 and one or more tube lenses 722 to the image plane of a detector 724. The excitation light emitted by the light source is scattered from the sample, as indicated by dashed arrows, such as dashed arrow 726, and any excitation light scattered back through the objective lens or lenses is reflected from the surface of the dichroic mirror or absorbed by the emission filter 720. Thus, the optical components of the fluorescence microscope primarily image fluorescent light, emitted by fluorophores within the sample, at the detector.

Figure 8B:
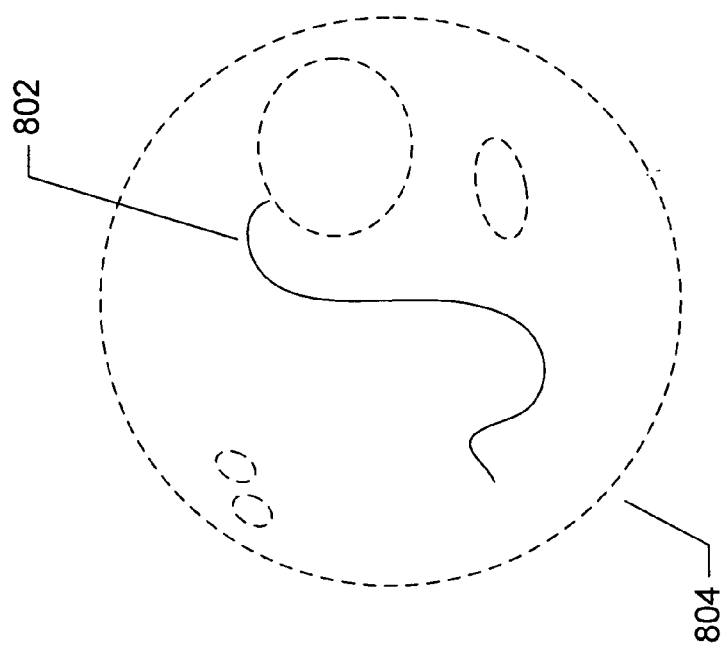
FIGS. 8A-B illustrate the large contrast obtained for biological samples by fluorescence microscopy.
Figure 8A:
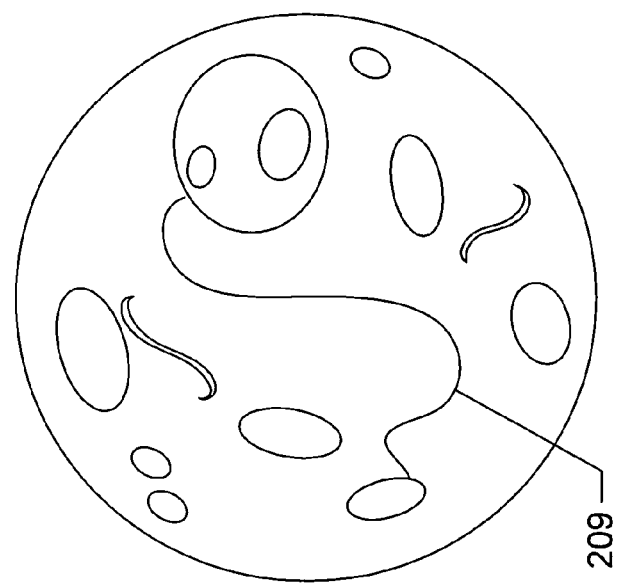

FIGS. 8A-B illustrate the large contrast obtained for biological samples by fluorescence microscopy. FIGS. 8A-B use the same illustration conventions used in FIGS. 2A-B. FIG. 8A shows the same disk-like portion of the object plane within a biological sample as shown in FIG. 2A. FIG. 8B illustrates an image generated by fluorescence microscopy from the object plane within the biological sample when structure 209 on the biological sample has been labeled by GFP or another biological or chemical fluorophore. The fluorescence microscope principally detects fluorescent emission from the labeled structure, which appears at high contrast 802 with respect to other features of the sample in the image produced by fluorescence microscopy 804.

Figure 9:
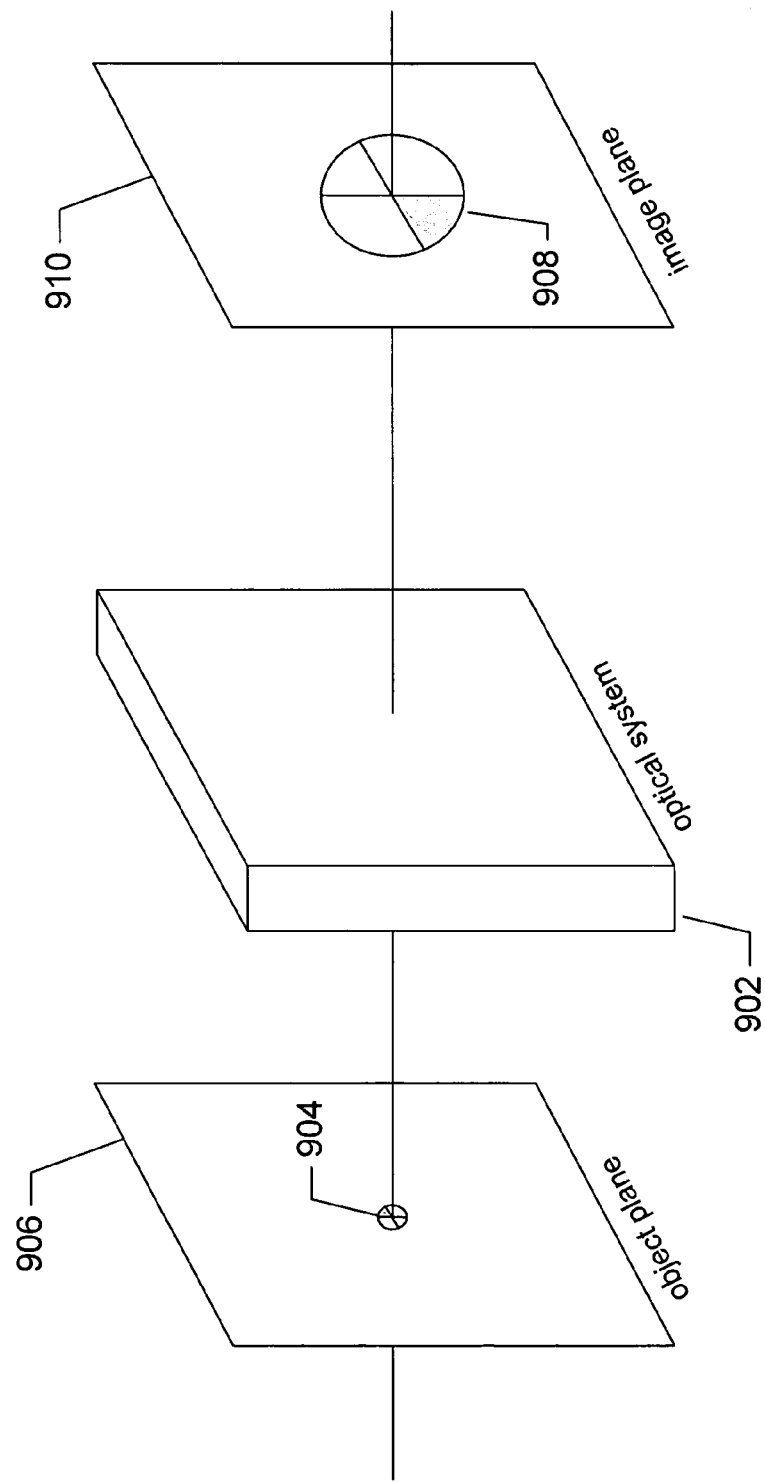
FIG. 9 provides an abstract representation of an optical system, such as a standard optical microscope or fluorescence microscope.

FIG. 9 provides an abstract representation of an optical system, such as a standard optical microscope or fluorescence microscope. In general, the optical system 902 focuses and magnifies an input image 904 within the object plane 904 to form a magnified image 908 on an image plane 910. The object plane is, in microscopy, generally a plane normal to the optical axis within a sample and the image plane, also normal to the optical axis, is generally a CCD detector, the retina of a human eye, or an image plane within another type of detector.

Figure 10:
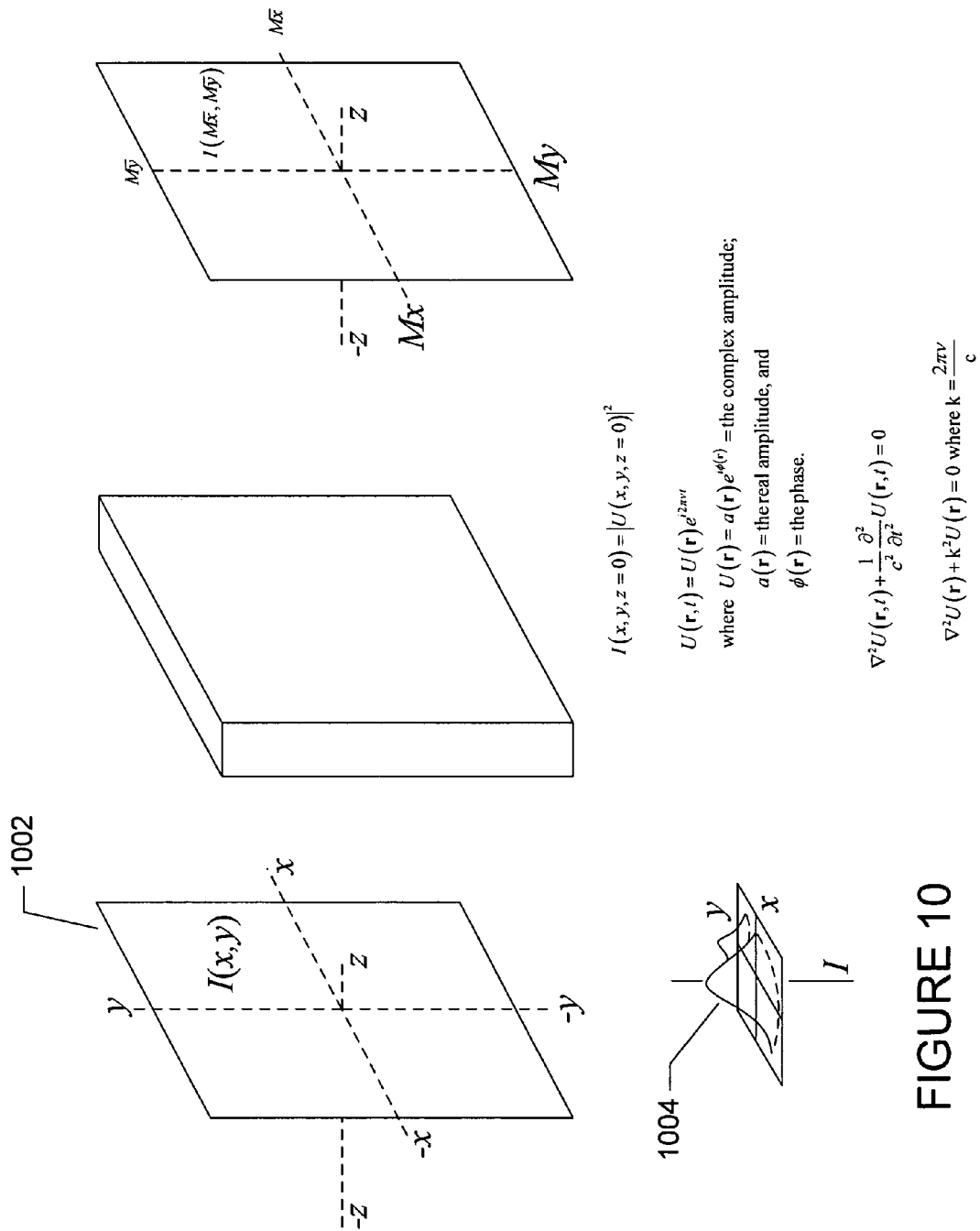
FIGS. 10-12 illustrate a mathematical model for optical imaging.
Figure 11:
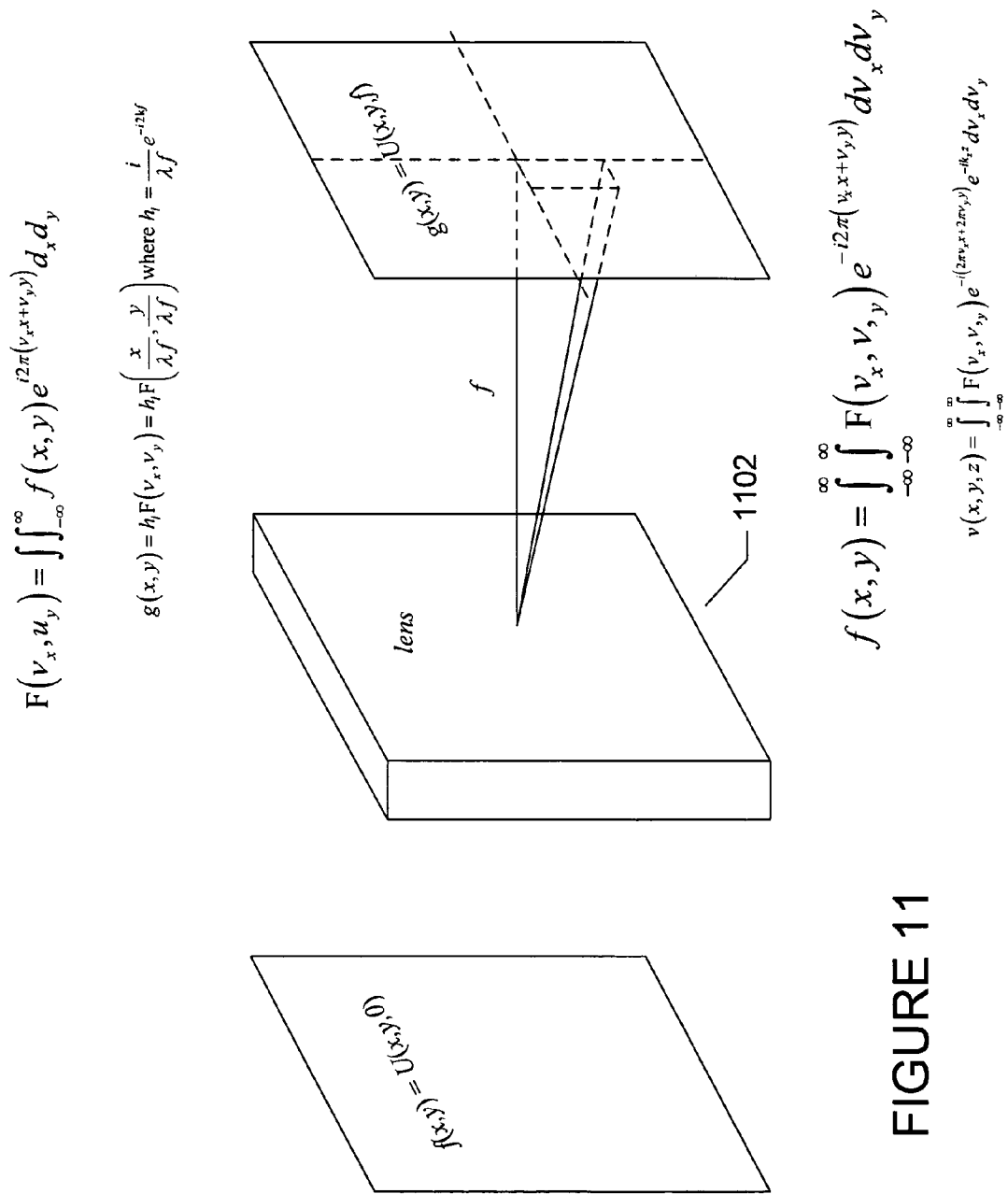
Figure 12:
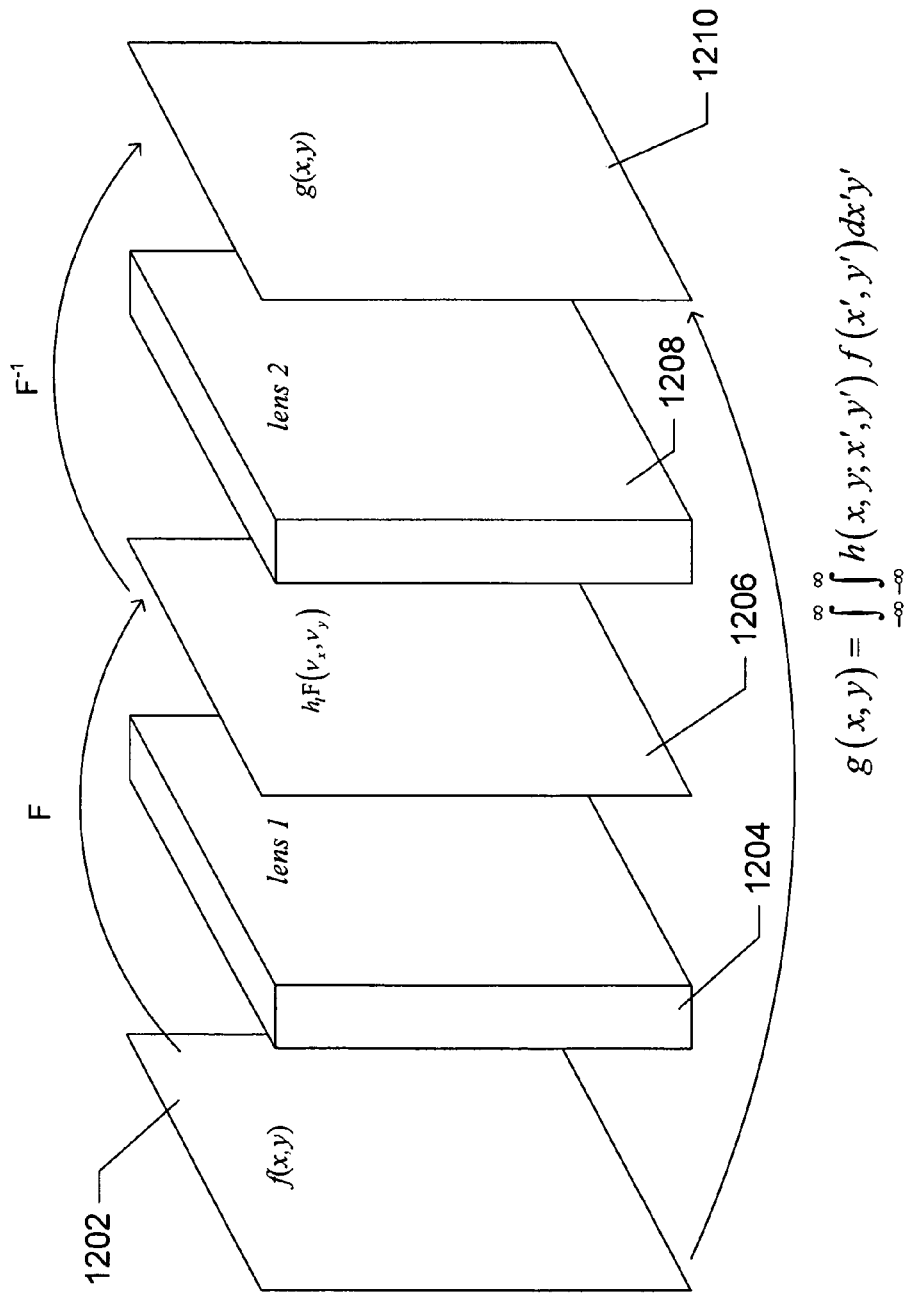

FIGS. 10-12 illustrate a mathematical model for optical imaging. FIGS. 10-12 use the same illustration conventions, or similar illustration conventions, as used in FIG. 9. As shown in FIG. 10, the input image at the object plane 1002 can be described as a function $I(x,y,z=0)$ where $x$ and $y$ are orthogonal dimensions in the image plane and z corresponds to the optical axis normal to the image plane and optical-system components. The value of the function I(x,y) represents the intensity of light at each point in the object plane, and can be thought of as a surface 1004. The input image, I(x,y,z=0) can be mathematically modeled as the squared magnitude of a wave function:

$$I(x,y,z=0) = |U(x,y,z=0)|^2$$

The wave function can be expressed, in vector form, for monochromatic light of frequency v, as:

$$U(r,t) = U(r)e^{i2\pi vt}$$

where
  $U(r) = a(r)e^{i\phi(r)}$ = the complex amplitude;
  a(r) = the real amplitude, and
  $\phi(r)$ = the phase.

The function U(r,t) is a function that satisfies a differential equation known as the "wave equation:"

$$\nabla^2 U(r,t) + \frac{1}{c^2}\frac{\partial^2}{\partial t^2} U(r,t) = 0$$

and a differential equation known as the "Helmholtz equation:"

$$\nabla^2 U(r) + k^2 U(r) = 0$$

where $k = \frac{2\pi v}{c}$

U(r) is the time-invariant complex amplitude for the light wave and U(r,t) is a time-dependent model of the light wave. The image I(x,y) is time invariant, depending only on the complex amplitude U(r). The wave function is a scalar function of position and time, and is therefore not a complete mathematical for light, but is adequate for explaining many optical phenomena.

As shown in FIG. 11, a lens 1102 can be modeled as an optical system that transforms an input function $f(x,y) = U(x,y,0)$ to an output function $g(x,y) = U(x,y,f)$. The input function $f(x,y)$ and output function g(x,y) are equivalent to the time-independent wave functions for a light wave at the object plane and image plane, respectively. The input function $f(x,y)$ can be modeled as a superposition of harmonic functions of the spatial dimensions x and y:

$$f(x,y) = \int_{-\infty}^{\infty}\int_{-\infty}^{\infty} F(v_x, v_y)e^{-i2\pi(v_x x + v_y y)} dv_x dv_y$$

The coefficients $F(v_x, u_y)$ are obtained by the Fourier transform:

$$F(v_x, u_y) = \iint_{-\infty}^{\infty} f(x,y)e^{i2\pi(v_x x + v_y y)} dx dy$$

The operation of a lens on the input function $f(x,y)$ to produce the output function g(x,y) can be expressed as:

$$g(x,y) = h_l f(v_x, v_y) = h_l F\left(\frac{x}{\lambda f}, \frac{y}{\lambda f}\right)$$

where $h_l = \frac{i}{\lambda f} e^{-i2kf}$

In other words, the output image is a frequency-domain image generated by focusing harmonic components of the input image $f(x,y)$ to different points in the output image g(x,y). The output image g(x,y) is a Fourier transform of the input image $f(x,y)$.

FIG. 12 illustrates a mathematical model for an imaging optical system. An input image 1202 is transformed, by a first lens 1204 to a frequency-domain image 1206, as discussed above, and a second lens 1208 transforms the frequency-domain image 1206 to a final, spatial-domain output image g(x,y) 1210 by a process modeled as a second, inverse Fourier transform. The entire process can be more mathematically modeled as a convolution:

$$g(x,y) = \int_{-\infty}^{\infty}\int_{-\infty}^{\infty} h(x,y;x',y')f(x',y') dx' dy'$$

where h(x,y;x',y') is the impulse-response function for the optical system. As discussed in greater detail below, the output image can be computed as a convolution of the impulse-response function with the input image. Note that, for an optical system that magnifies the input image, input-image coordinates x' and y' correspond to output-image coordinates x=x'M and y=y'M, where M is the magnification factor.

Figure 13:
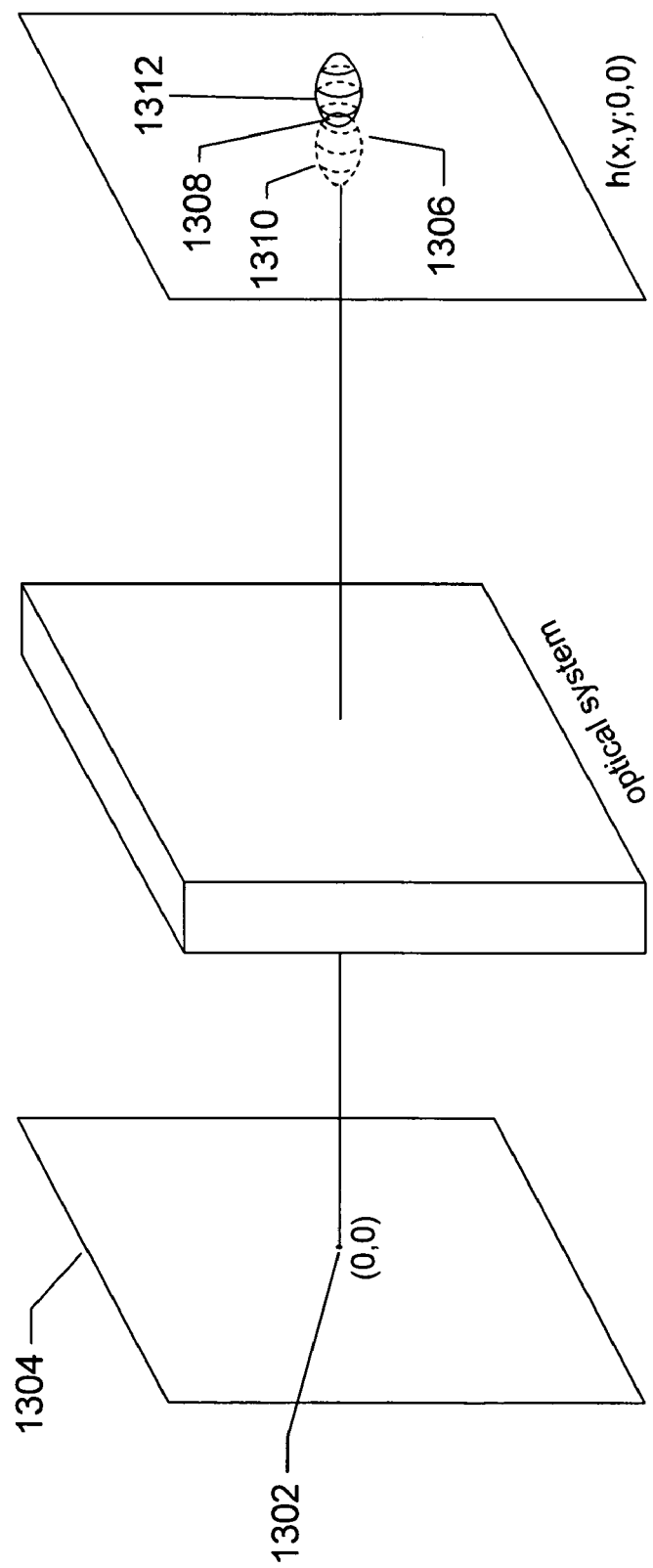
FIGS. 13-16 illustrate characteristics of the impulse-response function h(x,y; x',y') discussed with reference to FIG. 12.

FIGS. 13-16 illustrate characteristics of the impulse-response function h(x,y;x',y') discussed with reference to FIG. 12, above. As shown in FIG. 13, the impulse-response function h(x,y;0,0), corresponding to the point (0,0) 1302 on the object plane 1304, is a two-lobed intensity distribution 1306 with circular cross-section 1308 in the image plane, a first lobe 1310 of the two-lobed distribution is cylindrically symmetric about the z-axis and projects from the image plane back toward the object plane, and the second lobe 1312, also cylindrically symmetric about the optical axis, projects outward, away from the object plane from the circular cross-section 1308 in the image plane. In FIG. 13, and in subsequent figures, the illustrated surface of the impulse-response function is a surface of constant intensity. The idealized impulse-response function extends without bound through real space. However, at a particular distance in any direction from the point (0,0) in output-image space, the intensity of the input-response function falls to an arbitrarily low value, so that, for example, a constant-intensity surface can be constructed to describe the impulse-response function for an intensity level below which intensity is undetectable. The impulse-response function can be considered to be a function that maps a point source in the object plane to an intensity distribution in output-image space, or, alternatively, as the image of the point source. The output image becomes increasingly unfocused with distance, in the z direction, from the image plane. Blurring of the image of the point source with distance is reflected in the initial increase in the radii of circular cross-sections of the impulse-response function with increasing distance from the output-image plane. Subsequent decrease in the radii of circular cross-sections with greater distance from the image plane is related to the decreasing intensity with distance from the origin (0, 0) in the image plane.

Figure 14:
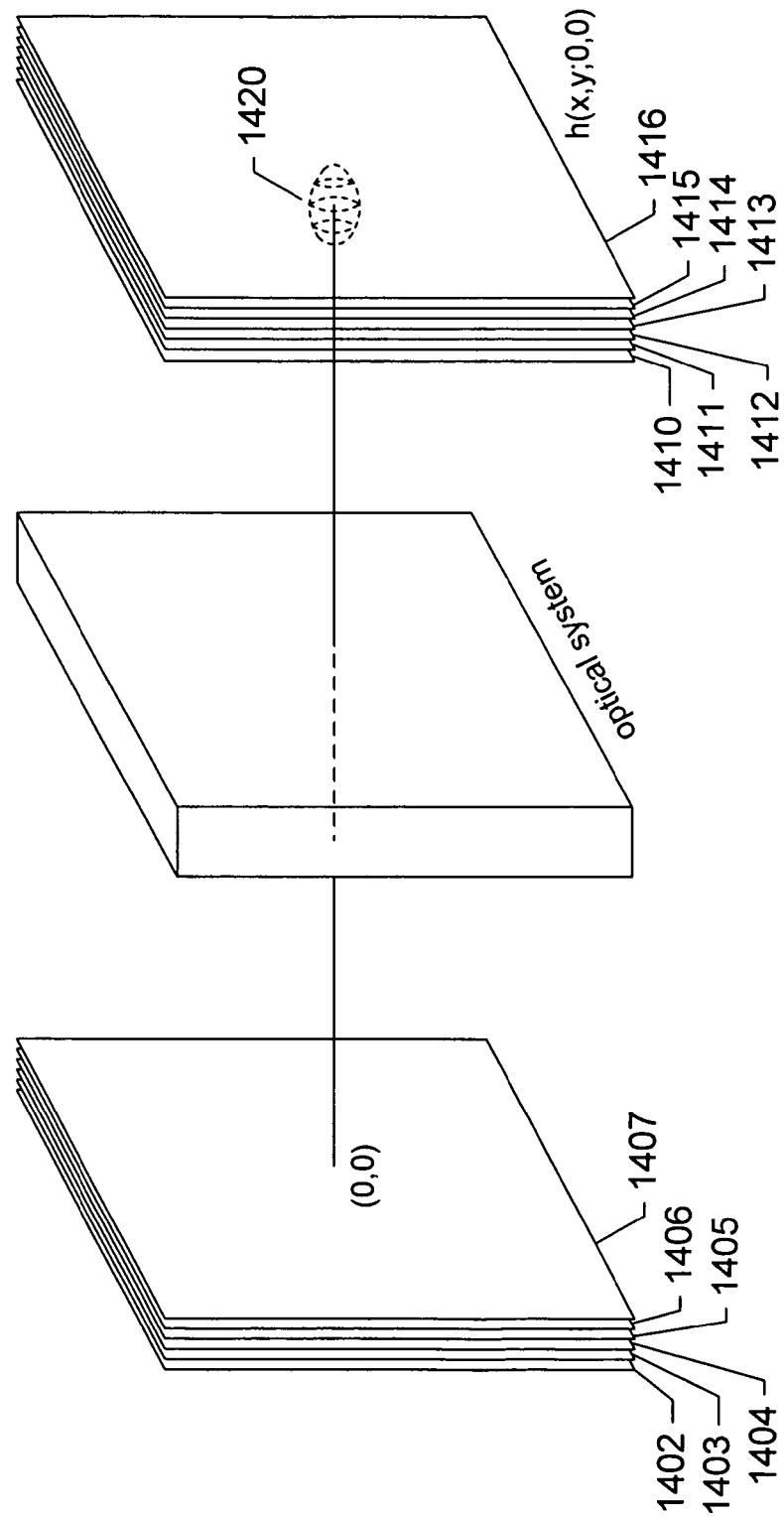

FIG. 14 illustrates a constant-intensity surface of the impulse-response function in three-dimensional output-image space. As shown in FIG. 14, fluorescence microscopists commonly image a series of object planes 1402-1407 within a sample by changing the distance between the sample and the objective lens after acquiring each image of the series of images at a fixed position with respect to the objective. This produces a corresponding set of output images 1410-1416. When a set of input images about the point (0,0,0) in three-dimensional input-image space is imaged by the optical system, the three-dimensional impulse-response function corresponding to the point (0,0,0) is a cylindrically symmetrical ellipsoid 1420 in three-dimensional output-image space. In an aberration-free optical system with continuous imaging in the x, y, and z directions, the impulse-response function h(x,y; 0,0) is spherically symmetric about the point (0,0,0) in output-image space. Again, the impulse-response function extends outward from the point (0,0,0) in output-image space through all of real space. However, the intensity decreases with increasing distance from the point (0,0,0), so that an ellipsoid or sphere of constant intensity can be constructed to represent the impulse-response function.

Figure 15:
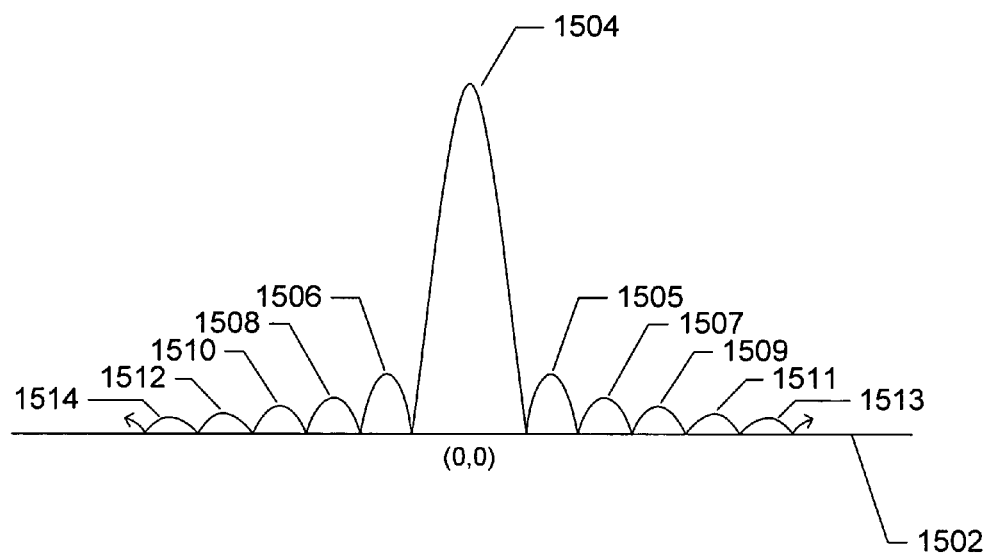
Figure 16:
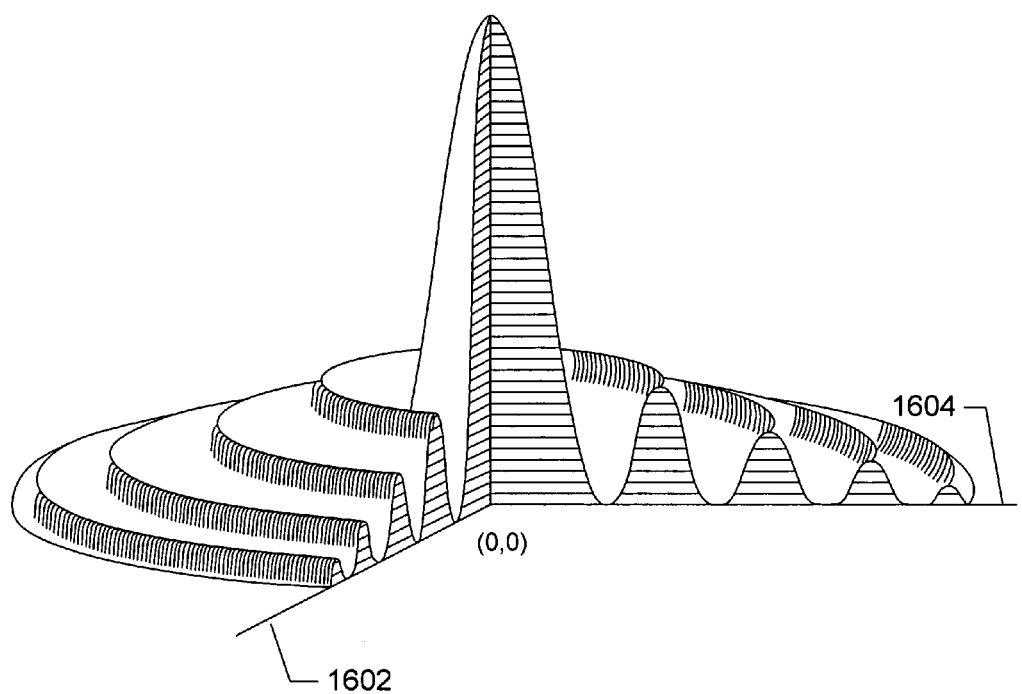

FIG. 15 illustrates the impulse-response function in one dimension within the output-image plane. The horizontal axis 1502 is a line in the output-image plane passing through the origin (0,0). The theoretical impulse-response function has a tall, relatively narrow central peak 1504 with secondary peaks of decreasing height 1505-1514 extending in both directions away from the central peak. The height of the impulse-response curve corresponds to intensity and the horizontal axis 1502 corresponds to linear distance from the origin in the output-image plane. The theoretical impulse-response function is proportional to the square of the $J_1$ Bessel function. FIG. 16 provides a representation of the impulse-response function in three-dimensional space, where the two horizontal axes 1602 and 1604 lie in the plane of the output-image plane and cross at the origin (0,0) and the height, at any point on the surface of the impulse-response function corresponds to the intensity observed at a corresponding position on the image plane. An image of the impulse-response function produced by an optical system appears to be a central bight disk, corresponding to the central peak of the impulse-response function, with concentric rings of increasing radius corresponding to the rings or ridges surrounding the central peak.

Figure 17:
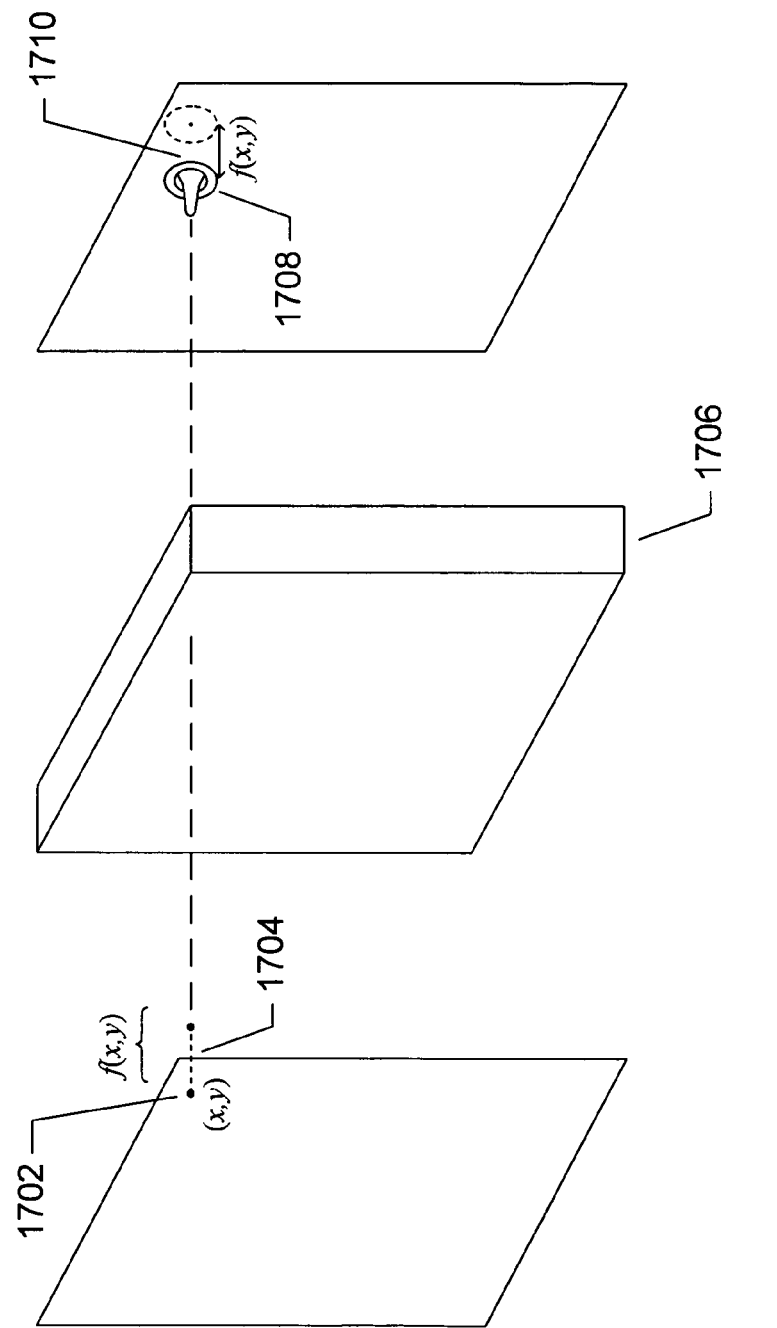
FIGS. 17-18 illustrate a convolution-based mathematical model, discussed above with reference to FIG. 12, for computing an output image of an optical system from the image input to the optical system and the impulse-response function for the optical system.
Figure 18:
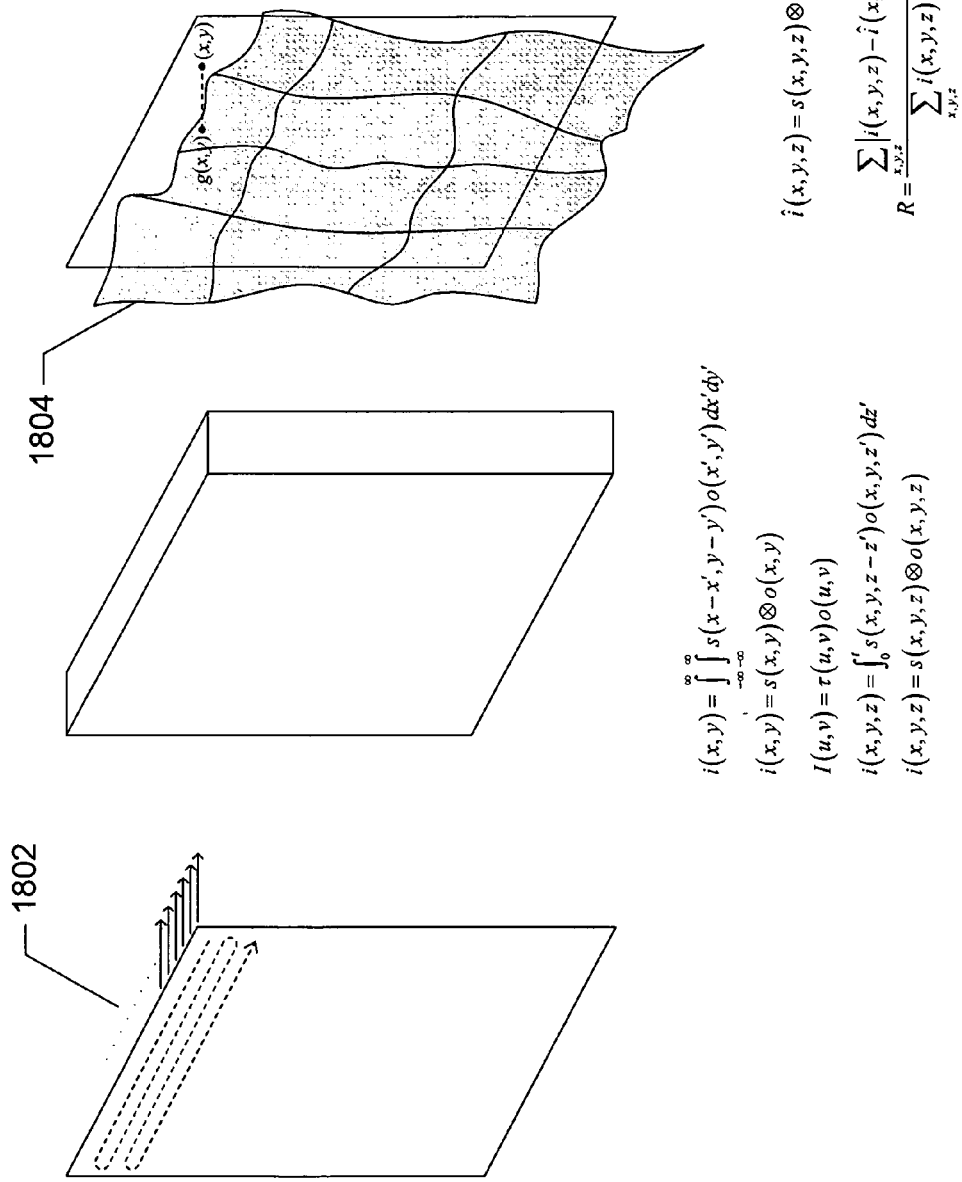

FIGS. 17-18 illustrate a convolution-based mathematical model, discussed above with reference to FIG. 12, for computing an output image of an optical system from the image input to the optical system and the impulse-response function for the optical system. Note that the impulse-response function illustrated in FIGS. 13-16 is a theoretical impulse-response function of an aberration-free optical system. However, in all practical implementations of optical systems, it is not possible to compute an impulse-response function for the system, due to many complex aberrations that are difficult to mathematically model. The impulse-response function is experimentally determined by imaging tiny light sources in the object plane. It should also be noted that, in practical systems, the impulse-response function may vary with respect to location of point sources in the input-image plane. However, in the following discussion, the impulse-response function is generally assumed to be position independent.

FIG. 17 illustrates the basic operation that is repeated over the entire area of the input image plane in order to compute the output image by the convolution method discussed above with reference to FIG. 12. A given point (x,y) 1702 in the input-image plane, to which a wave-function amplitude ƒ(x,y) 1704 corresponds, is regarded as a point source of light of amplitude ƒ(x,y), light emitted from which passes through the optical system 1706 and is transformed by the optical system into the corresponding impulse-response function 1708 multiplied by the amplitude ƒ(x,y) 1710. As shown in FIG. 18, when the basic operation show in FIG. 17 is repeated for all points in the input-image plane 1802, the sum of all the input-response functions generated by a light source at each point forms a surface 1804, where the height of the surface g(x,y) above a corresponding point (x,y) in the output-image plane is the intensity of the output image at that point. Thus, changing notation, the output image i(x,y) is computed as convolution of the impulse-response function, or point-spread function ("PSF"), s(x-x', y-y'), with the input image o(x',y'). In mathematical notation:

$$i(x, y) = \int_{-\infty}^{\infty}\int_{-\infty}^{\infty} s(x-x', y-y')o(x', y')dx'dy'$$

$$i(x, y) = s(x, y) \otimes o(x, y)$$

This convolution operation becomes a multiplication operation in the frequency domain:

$$I(u,v) = \tau(u,v)o(u,v)$$

where I(u,v) is the frequency-domain transform of the output image i(x,y); τ(u,v) is the optical transfer function that is the Fourier transform of the PSF; and O(u,v) is the frequency-domain transform of the input image o(x,y). When three-dimensional imaging is considered, these relationships can be expressed as:

$$i(x,y,z) = \int_0^i s(x,y,z-z')o(x,y,z')dz'$$

$$i(x,y,z) = s(x,y,z) \otimes o(x,y,z)$$

In deconvolution microscopy, an estimate of the input image o(x,y,z), ô(x,y,z), is convolved with the PSF to produce a corresponding computed image î(x,y,z):

$$\hat{i}(x,y,z) = s(x,y,z) \otimes \hat{o}(x,y,z)$$

In general, convolution is carried out in the frequency domain, by a multiplication operation, and the corresponding frequency-domain entities are then transformed, by inverse Fourier transforms, back to their spatial-domain equivalents. An R factor, or residual, can be computed to reflect the difference between the computed image and the observed image:

$$R = \frac{\sum_{x,y,z} |i(x, y, z) - \hat{i}(x, y, z)|}{\sum_{x,y,z} i(x, y, z)}$$

The estimated input image can then be altered, by any of various techniques, such as a Newton-descent optimization technique, to produce a subsequent, better estimate of the input image, from which a corresponding output image can be computed and a new R factor generated. The process is iterated until the R factor falls below a threshold value, indicating that the estimated input image sufficiently closely represents the actual image input to the optical system.

Figure 19:
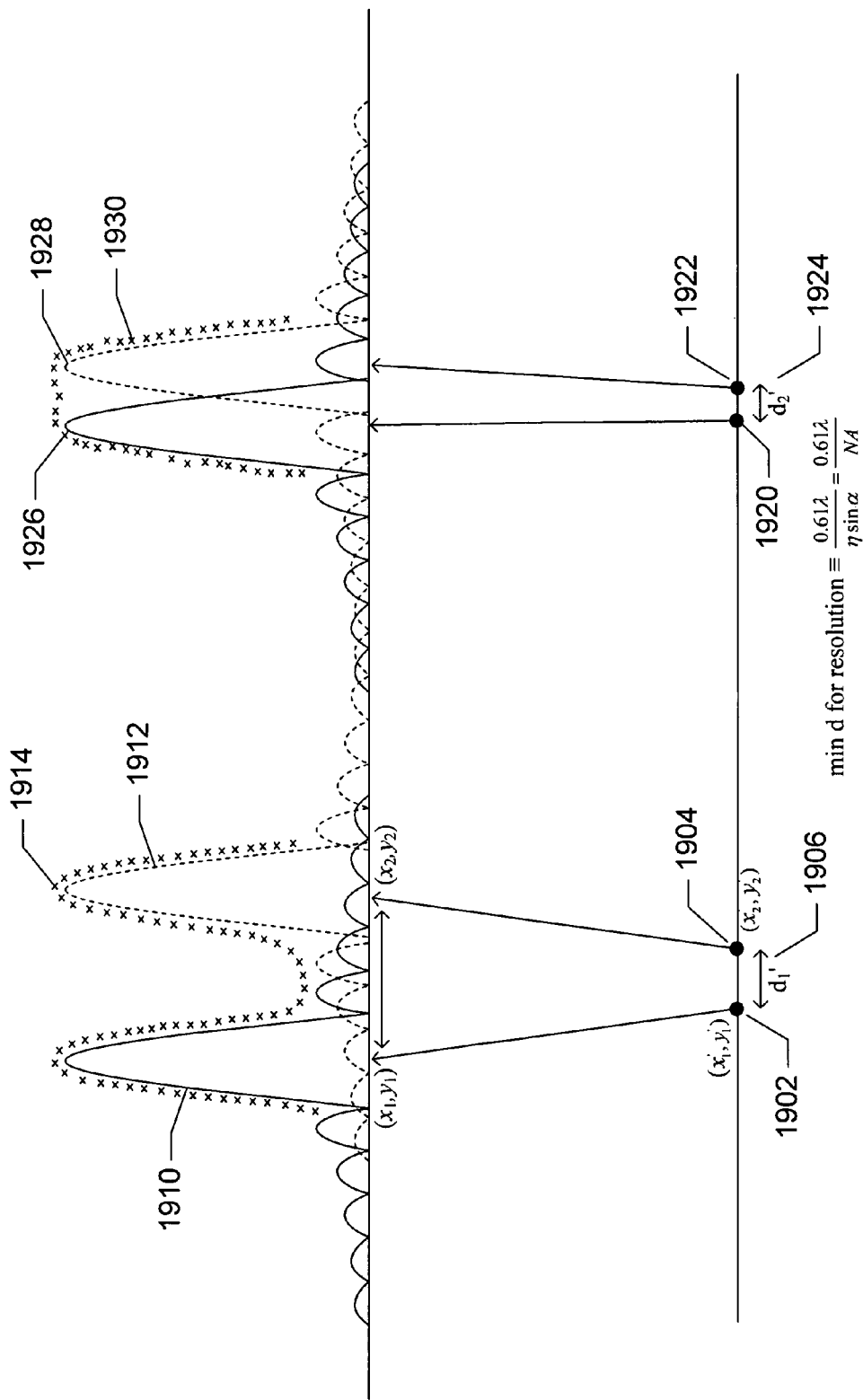
FIG. 19 illustrates the diffraction limit associated with of optical microscopy.

FIG. 19 illustrates the diffraction limit associated with of optical microscopy. Consider two points $(x_1',y_1')$ 1902 and $(x_2',y_2{}^{2'})$ 1904 in the object plane separated by distance $d_1'$ 1906. The images of these two points output from an optical system are two point-spread functions 1910 and 1912 centered at the output-image points $(x_1,y_1)$ and $(x_2,y_2)$ corresponding to points $(x_1',y_2')$ and $(x_2',y_2')$. The spreading of light from point sources of the input image into point-spreadfunction images at the output image is a diffraction-related phenomenon. When $d_1'$ is sufficiently large that the corresponding distance between the centers of the point-spread functions $d_1$ in the output image separates the point-spread-function distributions so that the sum of the two point-spread functions, represented in FIG. 19 by curve 1914, remains clearly bimodal, the images of points 1902 and 1904 in the output image can be distinguished from one another. However, when two points 1920 and 1922 in the input image are separated by a sufficiently small distance $d_2'$ 1924 that the images of the two points 1926 and 1928 in the output image overlap, with the sum of the two point-spread functions, represented by curve 1930 in FIG. 19, merging into a single peak, the two points 1920 and 1922 cannot be distinguished from one another in the output image. The minimum spacing, or maximum resolution, for traditional optical microscopy is generally regarded as:

$$\frac{0.61\lambda}{\eta \sin\alpha} = \frac{0.61\lambda}{NA}$$

where λ is the wavelength of light; and
NA is the numerical aperture for the optical system.
The minimum spacing in the input image corresponds to spacing between output point-spread functions at which the first left-hand zero point of the right-hand point-spread function coincides with the first right-hand zero point of the left-hand point-spread function. The minimum separation of features that can be imaged corresponds to approximately 200 nm for optical microscopy systems. The minimum spacing, or maximum resolution, is referred to as "the diffraction limit," since the point-spread-function images of point sources in the output image arise as a result of diffraction.

Until the 1990's, the diffraction limit discussed with reference to FIG. 19 was considered to be an absolute resolution limit for optical microscopy. However, during the past 20 years, various super-resolution fluorescence-microscopy techniques have been developed. FIGS. 20A-B illustrate a basis for super-resolution microscopy. FIG. 20A illustrates the effect of an optical system 2002 on light emitted in the direction of the z axis from a point 2004 on the object plane. As discussed above, the optical system spreads the intensity of the light over a disk-shaped point-spread function 2006 in the image plane. The point-spread function is thus viewed as a real-time smearing, or diffusion, of a point source by the optical system in output-image space. This smearing of point-like source light occurs for a number of different reasons. One important reason is that optical components, such as lenses, have finite apertures, and thus receive only a lower-angle portion of the non-coherent light emitted from a point source. Higher-angle emitted light rays fall outside the disk of a lens, and thus fall outside the optical path. The higher-angle rays that fail to be admitted to the optical components correspond to higher-frequencies in the frequency domain. Thus, optical components act as a spatial-frequency filter. Focusing of light by a second lens, modeled as an inverse Fourier transform, produces a spatial-domain image that is somewhat blurred, due to removal of high-frequency frequency-domain signals by optical components. Many additional factors contribute to dispersion of light in an output image represented by the point-spread function, including various types of aberrations inherent in optical components and other factors.

As illustrated in FIG. 20B, a second way to consider the point-spread function is that the point-spread function represents a probability distribution, with the intensities associated with points by the point-spread function corresponding to probabilities that individual photons will be deflected to that point by an optical system. Considered in this way, when a point-like source in the object plane is continuously imaged, and the continuous image accumulated, over time, by an electronic detector, such as a CCD detector, the accumulated intensity in the output image will be distributed according to the point-spread function. The point of highest accumulated intensity, in the output image, can be located to a precision equal to that of the resolution of the detector after accounting for the magnification factor of the optical system, when output light is collected for a sufficient period of time to generate a well-formed distribution of accumulated intensity in the image plane. This point corresponds to the object-plane location of a point source corresponding to the PSF in the image plane. It is theoretically possible to determine the location of point sources, using the centroids of corresponding PSF distributions in an output image, to a resolution of 1 nm or greater resolution. However, in order to achieve such precision, the light-emitting point sources must be separated by sufficient distance that their point-spread-function images, in the output image, do not appreciably overlap. Thus, while the location of sparsely distributed fluorophores can be determined to sub-diffraction-limit resolution, the fluorophores must be positioned within the sample so that the distance between any two fluorophores is greater than the diffraction-limit distance of between 180 and 200 nm, according to currently-practiced super-resolution imaging techniques.

Figure 21:
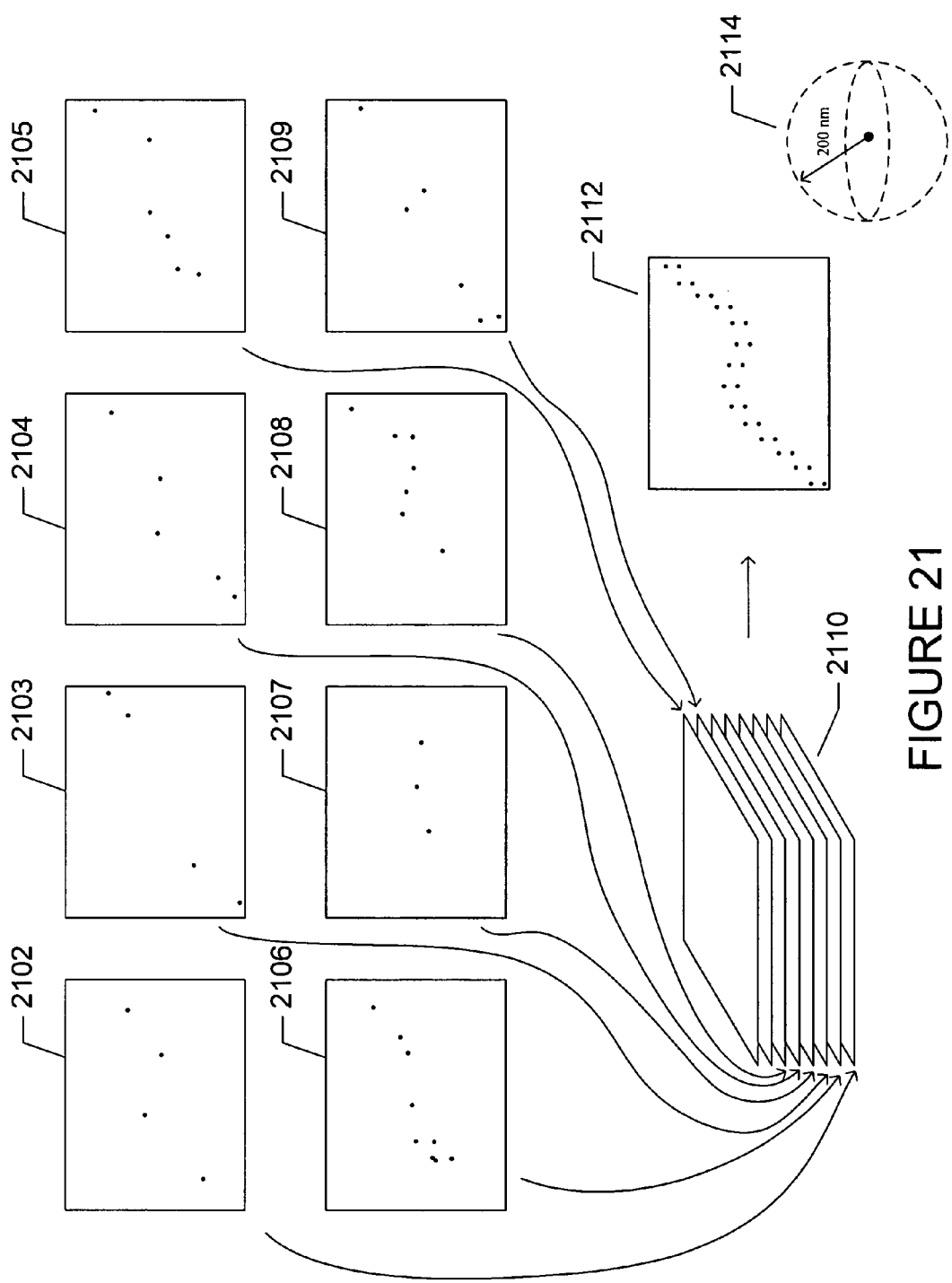
FIG. 21 illustrates currently-practiced super-resolution fluorescence microscopy.

FIG. 21 illustrates currently-practiced super-resolution fluorescence microscopy. A sample is labeled with fluorophores of sufficient density to ensure that, when the positions of the fluorophores are accurately determined, those positions will together produce an image of a structure, component, or organelle of interest to the fluorescence microscopist. Then, the sample is immobilized and a number of intermediate images are generated from the sample by, for each intermediate image, activating a small subset of the fluorophores and exciting fluorescent emission from the activated fluorophores. Only subsets of the fluorophores are activated in order to sufficiently separate fluorophores from one another to satisfy the above-discussed separation constraint. These techniques employ the characteristics of fluorophore labels, discussed above with reference to FIGS. 6A-C. Initially, the fluorophores are in a dark state, $F_D$. The sample is weakly illuminated with a frequency of light that converts a subset of the fluorophores from the state $F_D$ to an active state $F_A$. Activation of a small subset of the fluorophores is stochastic in nature. Activation is carried out with a weak illumination in order to ensure that the average spacing between fluorophores is significantly greater than the diffraction-limited distance, so that no two activated fluorophores are sufficiently closely spaced that their point-spread-function images overlap to the extent that the central peaks cannot be resolved, as discussed above with reference to FIG. 19, and therefore centroids for the fluorophore positions cannot be accurately computed. Following data collection for an intermediate image, the active fluorophores are then illuminated with a bright light of the specific wavelength most effective to bleach the active fluorophores, so that they cannot be again activated and do not fluoresce during data collection for subsequent intermediate images. As shown in FIG. 21, for example, each of intermediate images 2102-2109 are produced by collecting data from a different set of sparsely arranged, activated fluorophores. The intermediate images are then summed together 2110 to produce a final, composite high-resolution image 2112 that reveals a fluorophore-labeled structure, organelle, cellular component, or other feature in the sample. Again, the density of fluorophores simultaneously activated at any one time point needs to be such that each activated fluorophore is separated from all other activated fluorophores by a distance of at least 200 nm, as shown by the diffraction-limiting volume 2114 in FIG. 21.

Figure 22:
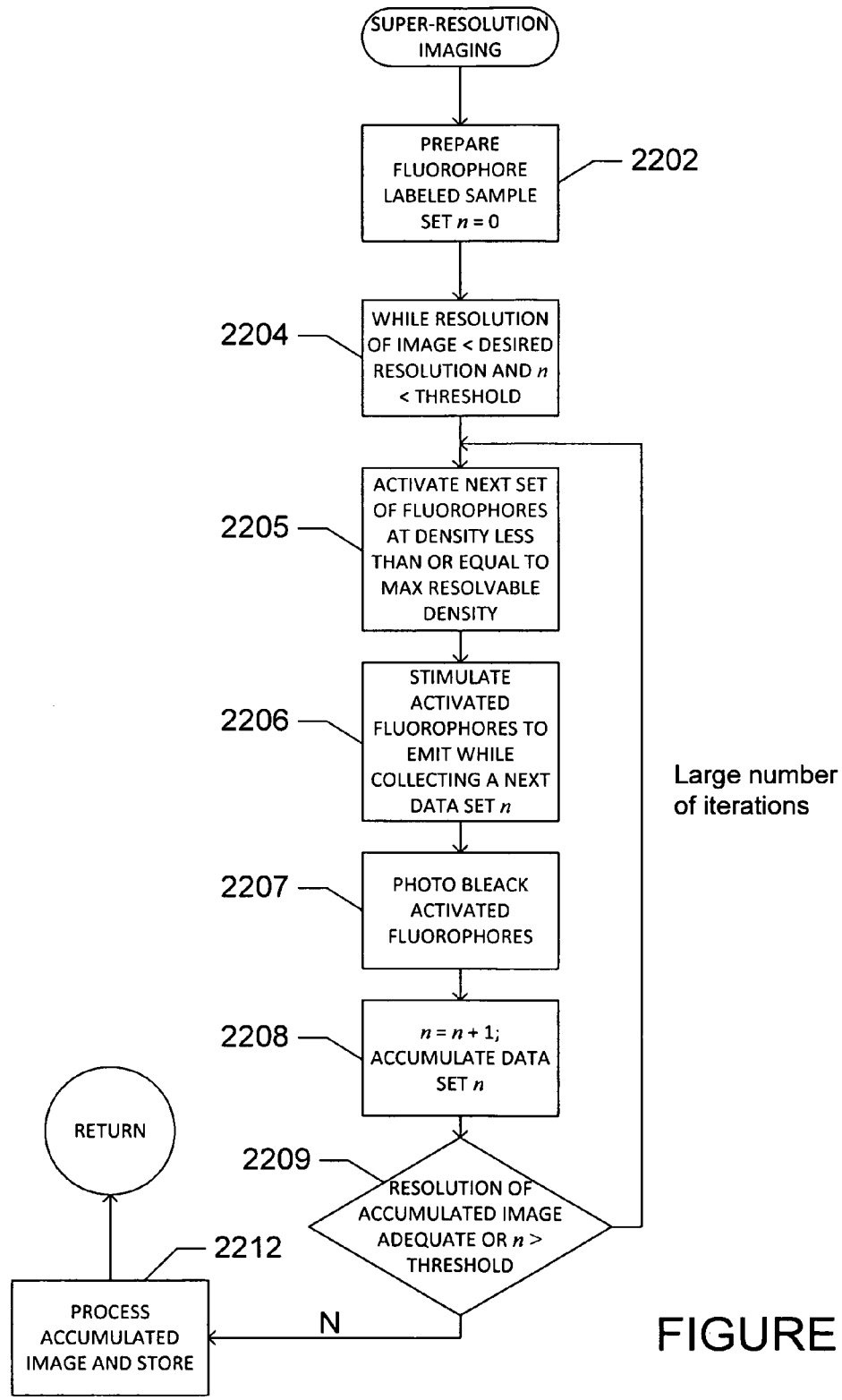
FIG. 22 provides a control-flow diagram that describes currently practiced super-resolution imaging techniques.

FIG. 22 provides a control-flow diagram that describes currently practiced super-resolution imaging techniques. In step 2202, a fluorophore-labeled sample is prepared. In the while-loop of steps 2204-2210, a number of intermediate images, as discussed above with reference to FIG. 21, are produced. In each iteration of the while-loop of steps 2204-2210, a next set of fluorophores is activated, in step 2205, with the density of the activated fluorophores less than or equal to the maximum resolvable density discussed above with reference to FIG. 21. In step 2206, fluorescent emission from the activated fluorophores is excited, and a next data set is collected, over time. In step 2207, activated fluorophores are brightly illuminated by light of an appropriate wavelength to bleach the activated fluorophores, removing that set of fluorophores from subsequent intermediate images. The intermediate image is produced from the collected data, in step 2208, by analyzing the data to find the centroids of the point-source images, as discussed above with reference to FIGS. 20B and 21. When sufficient data has been accumulated to generate a final image of adequate resolution, or the number of intermediate images produced exceeds a threshold number, as determined in step 2209, then the accumulated intermediate images are processed, in step 2212, to produce a final image, as discussed above with reference to FIG. 21 and the super-resolution imaging process terminates. Otherwise, control returns in step 2205 and a next intermediate image is produced.

Figure 23:
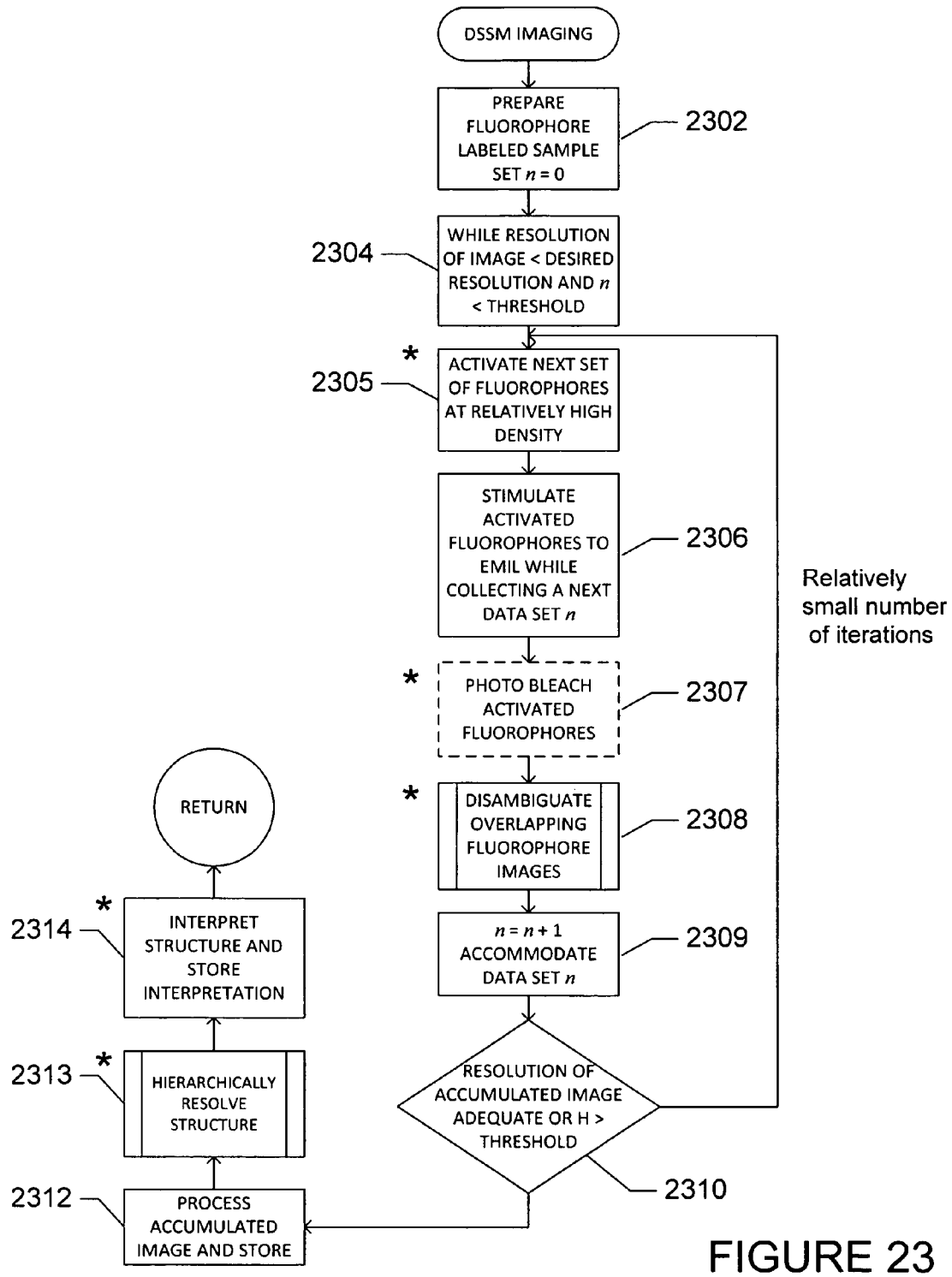
FIG. 23 provides a control-flow diagram that describes dense-stochastic-sampling imaging ("DSSI") that represents one embodiment of the present invention.

FIG. 23 provides a control-flow diagram that describes dense-stochastic-sampling imaging ("DSSI") that represents one embodiment of the present invention. Comparison of the control-flow diagram provided in FIG. 23 with the control-flow diagram provided in FIG. 22 reveals differences between the DSSI imaging method of the present invention and currently practiced super-resolution-imaging methods. Steps 2302, 2304, 2306, 2309, 2310, and 2312 are identical or similar to corresponding steps 2202, 2204, 2206, 2208, 2209, and 2212 in FIG. 22, and are not therefore again discussed. By contrast, steps 2305, 2307-2308, and 2313-2314 in FIG. 23 are novel or different from corresponding steps in FIG. 22, and are marked with "*" symbols to indicate these steps as points of differentiation between DSSI and currently-practiced super-resolution methods. In step 2305, a next set of fluorophores is activated for subsequent excitation and data collection to produce a next intermediate image. This step is similar to step 2205 in FIG. 22, with the important difference that, in DSSI imaging, the constraint that emitting fluorophores must be separated from one another by at least the diffraction-limiting distance of 200 nm is removed, and the fluorophores are activated at much greater density within the sample. This difference is especially significant for real-time imaging of living biological cells. By significantly increasing the density at which fluorophores are activated, the number of intermediate images needed to be produced and subsequently accumulated in order to construct a final image is significantly decreased. The decrease in intermediate images directly translates into a significant decrease in data-collection time, so that motile and shape-changing living cells can be imaged at high resolution by DSSI imaging, while, by currently practiced super-resolution techniques, the time required for data collection is sufficiently long that living cells may change shape or move sufficiently that the resulting image resolution may be low and the image quality poor. In addition, certain types of cells may be deleteriously affected, or killed, due to long exposure to fluorescence-activating and -exciting illumination, and that exposure can be significantly decreased by the reduction in intermediate images made possible by DSSI. In short, DSSI imaging techniques that represent embodiments of the present invention largely remove the density constraints for fluorophore activation, and thus significantly shorten data-collection times for both two-dimensional and three-dimensional imaging.

Step 2307 in FIG. 23, the photo-bleaching step, may be optional or less critical, unlike in corresponding step 2207 in FIG. 22 that illustrates currently practiced super-resolution techniques. Because fluorophores can be activated at significantly higher densities within the sample, and because fluorophore activation is stochastic in nature, repeated imaging of particular fluorophores in intermediate images during DSSI imaging have little consequence. In currently practiced techniques, by contrast, only a very few fluorophores can be activated for acquisition of each intermediate image, and it is therefore important that those imaged fluorophores are photo-bleached, or deactivated, so that redundant data is not collected in subsequent intermediate images. In other words, in DSSI imaging, collection of redundant data does not represent as significant an impact in overall data-collection times or in the number of intermediate images that need to be produced in order to achieve a desired final-image resolution as it does in currently practiced super-resolution techniques. Elimination of the photo-bleaching step, or a decrease in the level to which photo-bleaching needs to be carried out, may represent a significant decrease in the time required for data collection and imaging, and significantly reduces accumulated exposure of the sample to short-wavelength illumination. The combination of higher-density fluorophore activation, in step 2305, and elimination of the photo-bleaching step provides a fluorescence imaging methodology and system suitable for live-cell imaging. In addition, elimination of the photo-bleaching step may significantly simplify implementation of a DSSI imaging system. Rather than photo-bleaching activated fluorophores, certain embodiments of the present invention may deactivate activated fluorophores, using a reversibly activated fluorophore with characteristics described by FIG. 6C. Thus, in certain embodiments of the present invention, the photo-bleaching step may instead comprise a fluorophore-deactivation step. In other embodiments of the present invention, differential intermediate images may be computed by subtracting already-imaged fluorophore images from subsequent images, rather than deactivating activated fluorophores. In still additional embodiments of the present invention, deactivation and photo-bleaching are omitted entirely.

The ability to activate fluorophores at higher density and to eliminate or deemphasize photo bleaching arises from incorporation of an overlapping-fluorophore-distribution disambiguation step 2308 carried out in each iteration of the while-loop of steps 2304-2310. This is a computational, image-processing step that can detect overlapping images of fluorophores in intermediate images and correctly assign positions and relative intensities to fluorophores corresponding to overlapping fluorophore images. Because of the introduction of this computational, image-processing step into each iteration of the while-loop of steps 2304-2310, fluorophore activation can be carried out, for each fluorophore image, to generate activated fluorophores at much higher densities within the sample than can be accommodated by currently practiced super-resolution techniques. Once a final, composite image is produced from the intermediate images, in step 2312, an additional computational, image-processing step 2313 is used to further refine the image by hierarchically fitting geometrical shapes to fluorophore-location distributions within the composite image. Finally, in certain embodiments of the present invention, a final structure-interpretation processing step 2314 is employed to interpret image features. Steps 2308, 2313, and 2314 are discussed, in great detail, below.

Figure 24A:
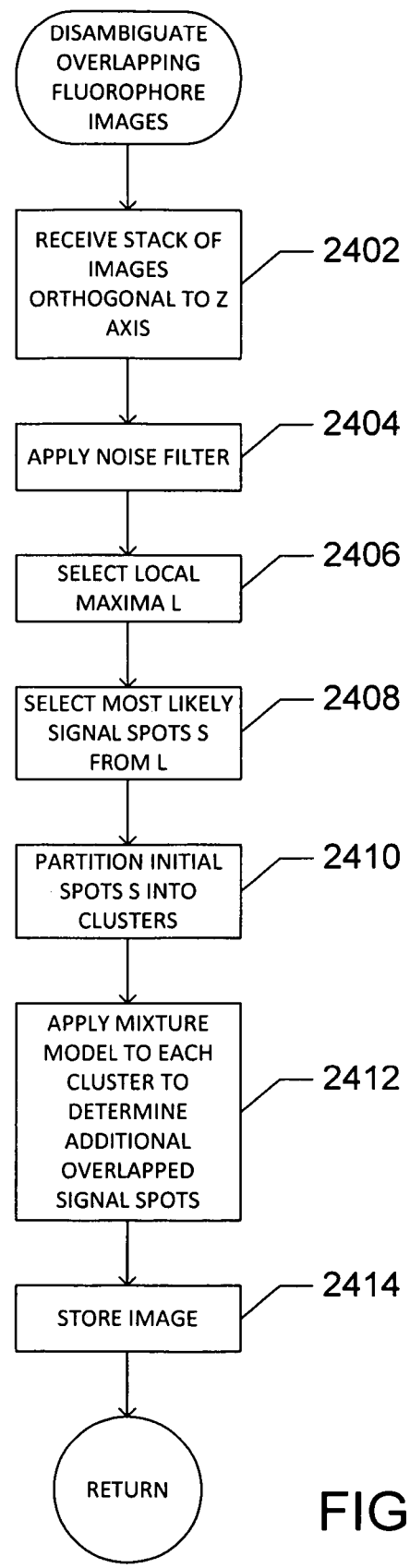
FIGS. 24A-B provide control-flow diagrams for the routine "disambiguate overlapping emitter images," called in step 2308 of FIG. 23, and the routine "apply mixture model," called by the routine "disambiguate overlapping emitter images," that are employed by one embodiment of the present invention.
Figure 24B:
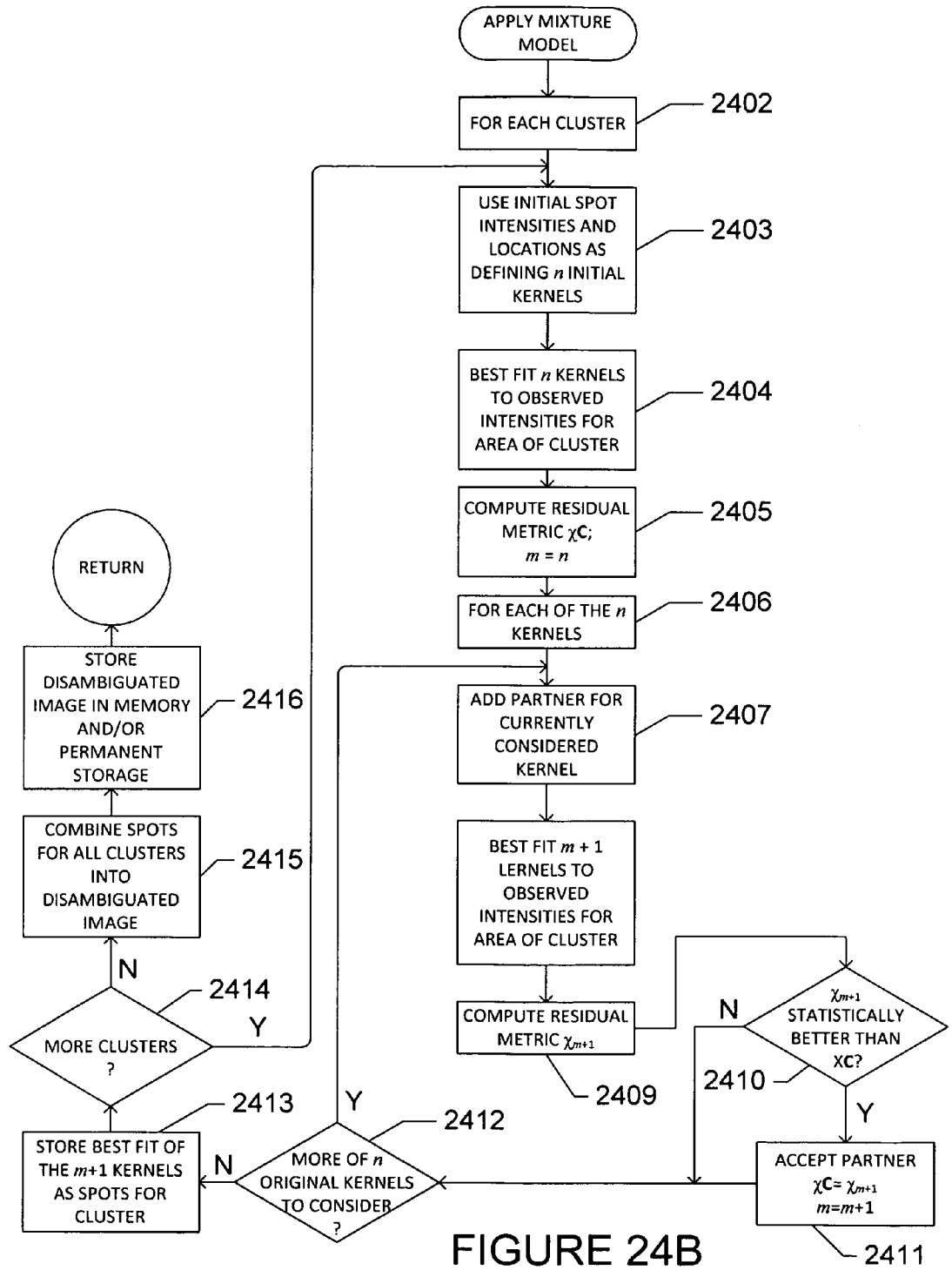

FIGS. 24A-B provide control-flow diagrams for the routine "disambiguate overlapping emitter images," called in step 2308 of FIG. 23, and the routine "apply mixture model," called by the routine "disambiguate overlapping emitter images," that are employed by one embodiment of the present invention. In discussing FIGS. 24A-B, references are made, below, to FIGS. 25-29. FIGS. 25-29 illustrate various steps used to disambiguating overlapping emitter images, according to one embodiment of the present invention.

Figure 25:
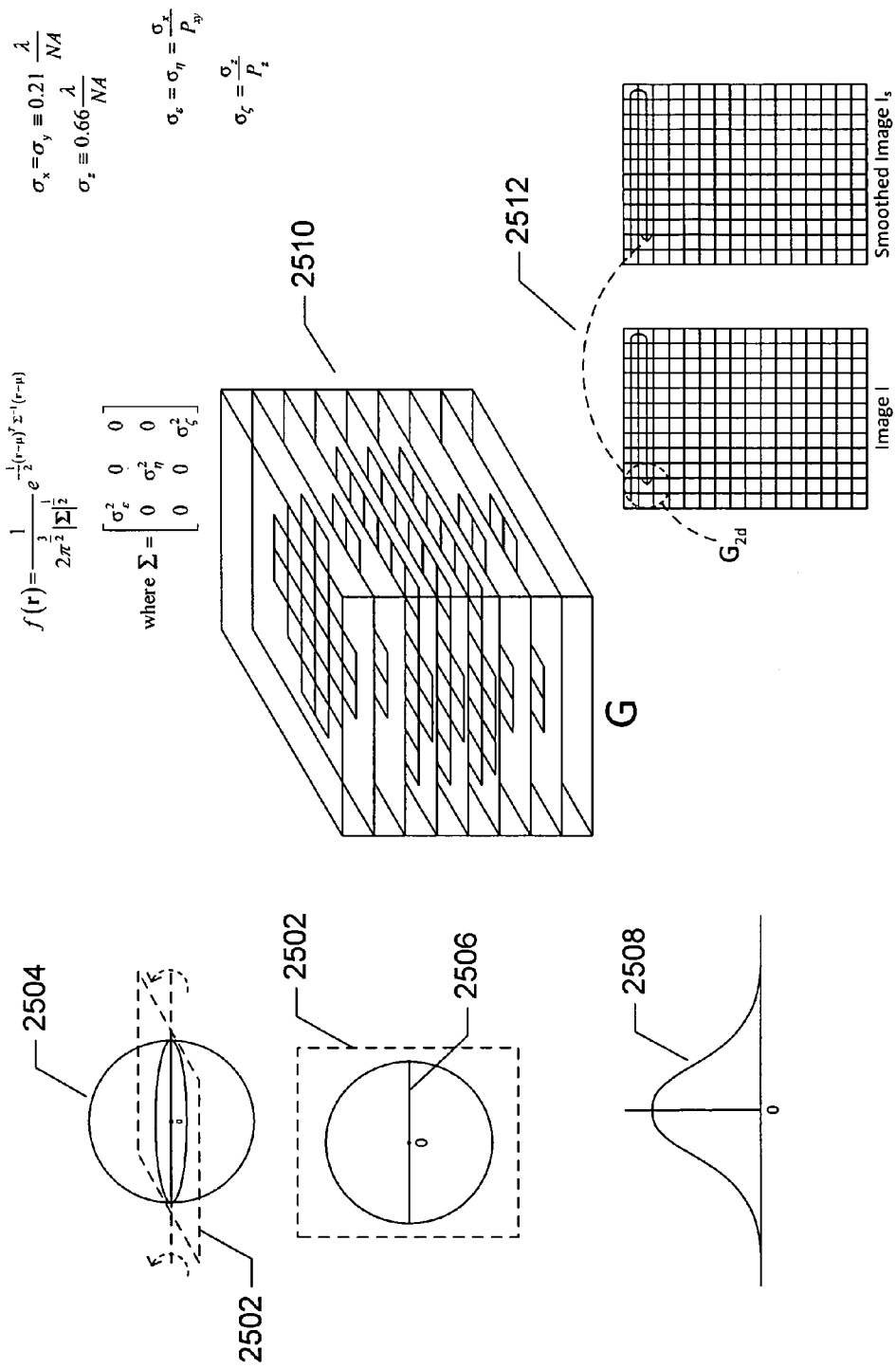
FIGS. 25-29 illustrate various steps used in disambiguating overlapping emitter images, according to one embodiment of the present invention.

Note that overlapping-fluorophore-image disambiguation is described generally, in the following discussion, to be applicable both to two-dimensional imaging as well as three-dimensional imaging. In both cases, stacks of images orthogonal to the optical axis, or z axis, and separated by a minimal z-axis translation, $\Delta z$, are employed. In step 2402, a stack of images orthogonal to the z axis is received. This may be a stack of intermediate images generated in a single iteration of the while-loop of steps 2304-2310 in FIG. 23 by collecting data from the sample over a range of z-axis translation of the sample relative through the objective lens. The received images may alternatively be a larger number of intermediate images orthogonal to the z axis produced for a wider range of z-axis positions in order to carry out three-dimensional imaging. Next, in step 2404, a noise filter is applied to the stack of images in order to filter noise from the raw images. FIG. 25 illustrates one type of noise filter employed in certain embodiments of the present invention. In certain embodiments of the present invention, a Gaussian noise filter is employed. The Gaussian filter is essentially a three-dimensional Gaussian distribution mathematically represented as:

$$f(r) = \frac{1}{2\pi^{\frac{3}{2}} |\Sigma|^{\frac{1}{2}}} e^{-\frac{1}{2}(r-p)^T \Sigma^{-1}(r-p)}$$

$$\text{where } \Sigma = \begin{bmatrix} \sigma_\varepsilon^2 & 0 & 0 \\ 0 & \sigma_\eta^2 & 0 \\ 0 & 0 & \sigma_\zeta^2 \end{bmatrix}$$

The diagonal matrix $\Sigma$ is equivalent to the covariance matrix. In one embodiment of the present invention, the object-space values for the standard deviations $\sigma_x$, $\sigma_y$, and $\sigma_z$ are defined to be $$0.21 \frac{\lambda}{NA}, 0.21 \frac{\lambda}{NA}, \text{ and } 0.66 \frac{\lambda}{NA},$$

and the corresponding image-space standard deviations are:

$$\sigma_\varepsilon = \sigma_\eta = \frac{\sigma_x}{P_{xy}}$$

$$\sigma_\zeta = \frac{\sigma_z}{P_z}$$

where $P_{xy}$ are pixel dimensions in the x,y object plane and $P_z$ are voxel dimensions in the z axis. In the expression for the Gaussian distribution, the vectors r and µ are both image-space vectors in the $\varepsilon$, $\eta$ and $\zeta$ coordinate system. The Gaussian distribution is spherically symmetric, with highest values at the center of the spherical distribution and with rapidly decreasing values with increasing distance, in all directions, from the center of the distribution. As shown in FIG. 25, if a plane section 2502 is taken through the spherical Gaussian distribution 2504 and a line 2506, or one-dimensional section, is taken from the plane section 2502, the distribution of values along the line would have the appearance of a bell-shaped curve 2508. A Gaussian filter used for image processing G 2510 is a discrete, pixel-based analog of a continuous three-dimensional Gaussian distribution. For image filtering, the raw image I is convolved with the Gaussian filter to produce a smooth image $I_s$:

$$I_s = G \otimes I$$

where the convolution is carried out by centering the Gaussian filter at each position in the original image, multiplying the values in the Gaussian filter with corresponding values in the original image, and then adding those product values to the smooth image 2512. Various techniques are used for computing the convolution when a Gaussian filter only partially overlaps the stacked images.

Figure 26:
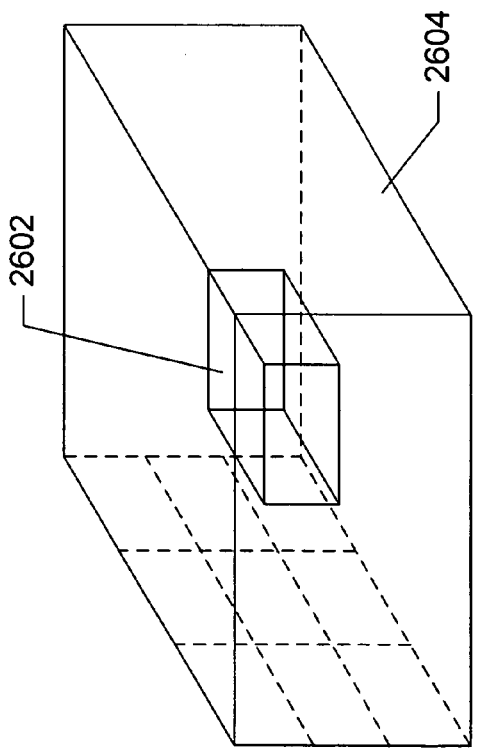

Next, in step 2406 of FIG. 24A, a set of local maxima L are extracted from the filtered image. Extraction of local maxima is illustrated in FIG. 26. Local maxima are defined, by the expression:

$$L = \{\zeta \epsilon I_{f_\alpha}(\zeta) | I_{f_x}(\zeta) > I(\zeta+t), \forall t_i \epsilon \{-1,0,1\}, t \neq (0,0,0)\}$$

Essentially, the criterion for selecting a particular pixel, or voxel, from the output image to be a candidate centroid for a fluorophore image, essentially a centroid of a PSF in the output image, is that the pixel or voxel 2602 has the highest intensity value with respect to all of its immediate neighbors 2604. In other words, voxel 2602 in FIG. 26 is centered within a 3×3×3 voxel volume 2604, and has the highest observed intensity value of all voxels within volume 2604. Initially, in step 2406 of FIG. 24A, voxels that have the highest intensity values with respect to their immediate neighbors are selected for inclusion in the set L containing local maxima. Next, in step 2408, the set L of local maxima is filtered to produce the set S of probable fluorophore-image centroids, or spots. The curvature at an image point $I(\zeta)$ is defined to be the determinate of the Hessian computed over a volume surrounding the image point $I(\zeta)$ $$\text{curvature } \kappa \text{ at } I(\zeta) = I(\varepsilon, \eta, \zeta) = \det(\mathcal{H}(E)) = \begin{vmatrix} \frac{\partial^2 I(\zeta)}{\partial \varepsilon^2} & \frac{\partial^2 I(\zeta)}{\partial \varepsilon \partial \eta} & \frac{\partial^2 I(\zeta)}{\partial \varepsilon \partial \zeta} \\ \frac{\partial^2 I(\zeta)}{\partial \eta \partial \varepsilon} & \frac{\partial^2 I(\zeta)}{\partial \eta^2} & \frac{\partial^2 I(\zeta)}{\partial \eta \partial \zeta} \\ \frac{\partial^2 I(\zeta)}{\partial \zeta \partial \varepsilon} & \frac{\partial^2 I(\zeta)}{\partial \zeta \partial \eta} & \frac{\partial^2 I(\zeta)}{\partial \zeta^2} \end{vmatrix}$$

A spot metric $S_{I(\zeta)}$ can be computed for each local maxima in set L as:

$$S_{I(\zeta)} = s_i = \overline{I}_i \kappa_i$$

where $\overline{I}_i$ is mean intensity within a rectangular volume with center i;

$\kappa_i$ is curvature at i; and $\overline{I}_i \epsilon L$

Figure 27:
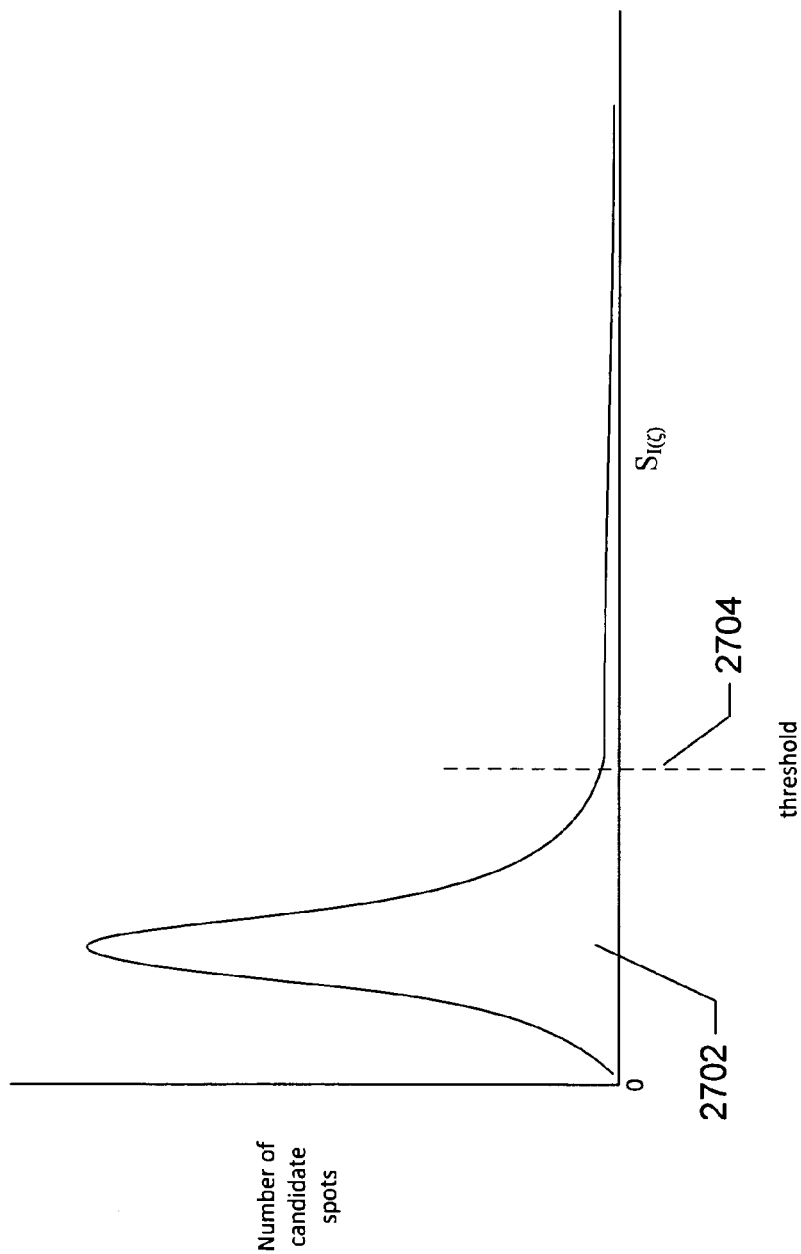

FIG. 27 shows a type of distribution of spot metrics computed for local maxima in the set L. Generally, a large majority of local maxima correspond to noise. Thus, the large peak 2702 at low spot-metric values in the distribution illustrated in FIG. 27 generally corresponds to image noise. To select centroids of fluorophore images, or spots, a threshold 2704 spot-metric value is selected to correspond to a spot-metric value at which the distribution curve flattens, past the large initial peak 2702. Those local maxima with spot metrics greater than the threshold value 2704 are selected as members of the set S, in step 2408 of FIG. 24A.

Figure 28:
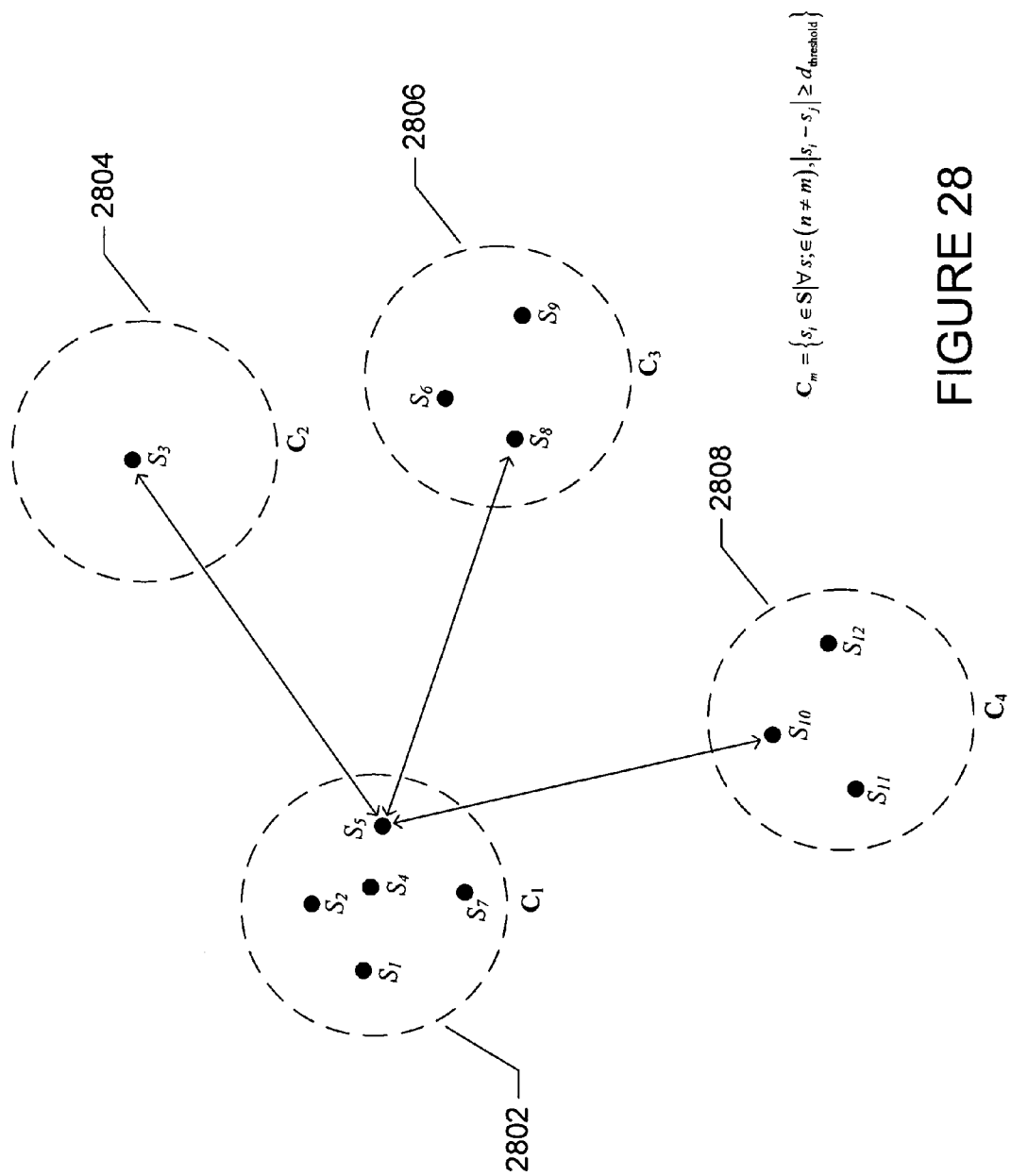

Next, in step 2410, the spots in set S are partitioned into clusters. FIG. 28 illustrates this partitioning of spots into spot clusters. The criteria by which the partitioning takes place can be described by:

$$C_m = \{s_i \in S | \forall s; \epsilon (n \neq m), |s_i - s_j| \geq d_{threshold}\}$$

The spots in a given cluster, such as cluster $C_1$ 2802, are all located at a distance greater than a threshold distance from the spots in all other clusters, such as clusters $C_2$ 2804, $C_3$ 2806, and $C_4$ 2804 in FIG. 28.

Figure 29:
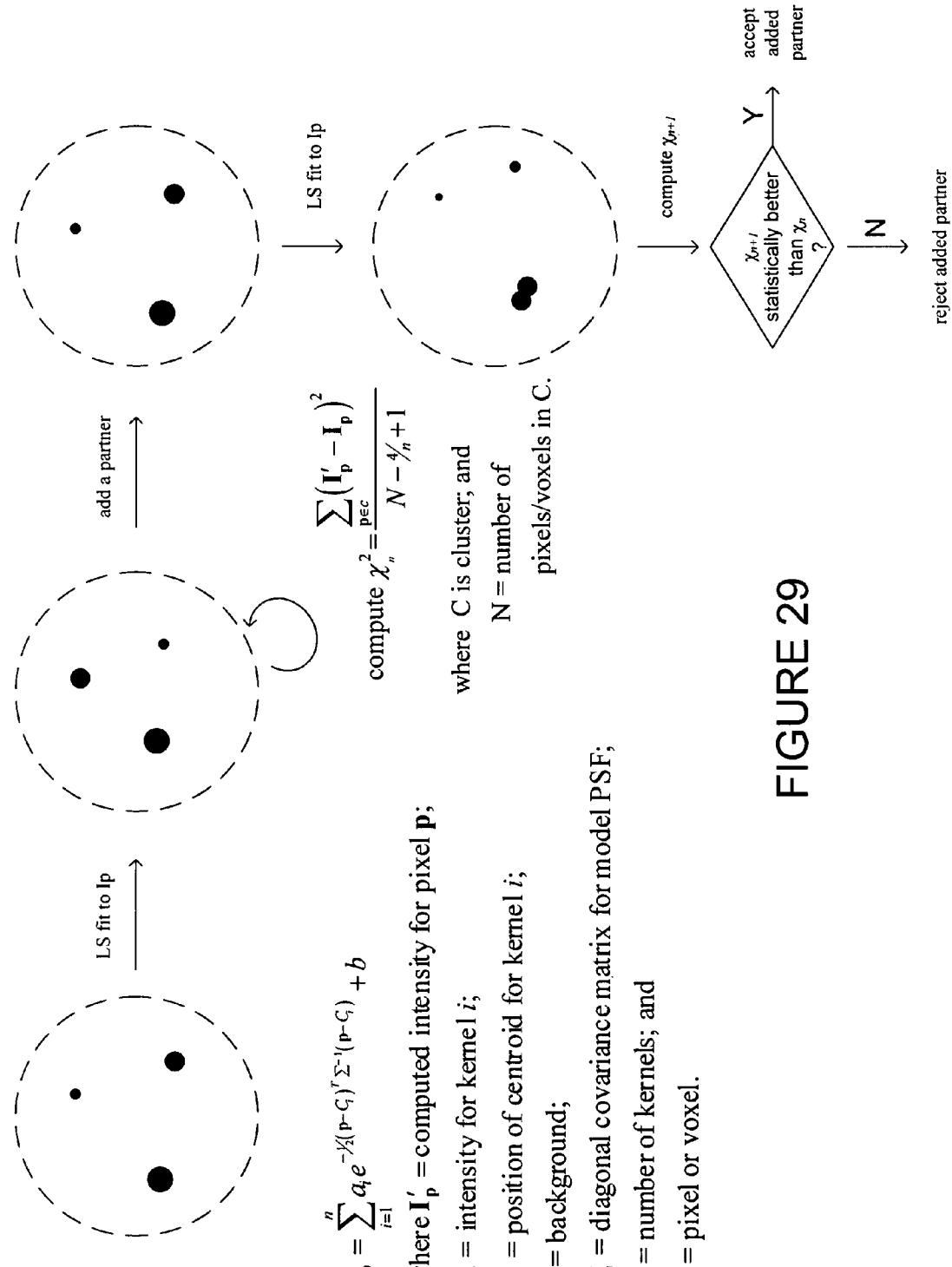

Then, in step 2412 of FIG. 24A, a mixture model is applied to the spots in each cluster in order to detect spots corresponding to overlapping fluorophore images, and the locations and intensities of these overlapping fluorophore images, or spots, are determined by an iterative computational procedure. This mixture-model computational method is described in greater detail, below. Finally, in step 2414 of FIG. 24A, the locations and intensities of all spots are stored electronically for subsequent processing, display on electronic display devices, or rendering as an initial image to various types of users for various reasons. FIG. 24B provides a control-flow diagram for the "apply-mixture-model" routine called in step 2412 of FIG. 24A. FIG. 29 illustrates the computational method described by FIG. 24B. The following discussion of FIG. 24B references FIG. 29.

The intent of applying the mixture model to a cluster of spots is to detect spots that represent overlapping fluorophore images, so that the overlapping images can be disambiguated and locations and amplitudes or intensities assigned to fluorophores corresponding to each of the overlapping fluorophore images. The mixture model is applied to each cluster in the for-loop of steps 2402-2414 in FIG. 24B. The intensities of pixels or voxels within a region associated with a cluster of spots can be computed based on the intensities and positions of centroids of each fluorophore image, or kernel, within the region associated with the cluster using the following mathematical model:

$$I'_p = \sum_{i=1}^{n} a_i e^{-\frac{1}{2}(p-C_i)^T \Sigma^{-1}(p-C_i)} + b$$

where
$I_p'$=computed intensity for pixel p;
$a_i$=intensity for kernel i;
$c_i$=position of centroid for kernel i;
b=background;
$\Sigma$=diagonal covariance matrix for model PSF;
n=number of kernels; and
p=pixel or voxel.

The fluorophore images, or PSFs, are modeled as Gaussian intensity distributions, in certain embodiments of the present invention. The positions and amplitudes of the known kernels within a region associated with a cluster can be fit, by a least-squares or other data-fitting technique, to the observed intensity of pixels or voxels within the area associated with the cluster by minimizing the difference between the computed intensities and observed intensities for pixels or voxels. In FIG. 29, a first cluster 2902 of spots, or kernels, with intensities and positions observed in the output image, are least-squares fit 2904 to the output image to produce an initial set of kernels 2906. A kernel is a parameterized model for the resolved image of a fluorophore. Statistic $\chi_n^2$, where the n represents the number of kernels currently considered to reside in the cluster, is computed for the set of kernels by:

$$\text{compute } \chi_n^2 = \frac{\sum_{p \in c}(I'_p - I_p)^2}{N - \frac{4}{n} + 1}$$

where
C is cluster; and
N=number of pixels/voxels in C.

The $\chi_n^2$ statistic is a type of residual that numerically describes how well the set of kernels explains the observed intensity in the acquired image. Next, a partner kernel is added, by random selection, to one of the kernels in the set of kernels. In FIG. 29, the partner kernel is shown as a dashed circle 2910 superimposed over the shaded disk 2912 representing the kernel. The kernels, including the partner kernel, are then fit, by a least-square fitting procedure or other data-fitting procedure 2914 to produce optimized amplitudes and positions 2916 for the kernels, including the partner kernel. A new statistic, $\chi_{n+1}^2$, is then computed 2918 and compared to the $\chi$ statistic computed for the previous least-squares-fit collection of kernels 2906. When $\chi_{n+1}^2$ is statistically better than $\chi_n^2$, as determined in the conditional step 2920 in FIG. 29, the added partner is accepted 2922, and represents, along with the kernel that it was originally partnered to, overlapping fluorophore images that were undetected in the original image. Otherwise, when $\chi_{n+1}^2$ is not statistically better than $\chi_n^2$, the added partner is rejected and removed from the set of kernels 2924. The $\chi_n^2$ statistics are distributed according to F statistics, and a suitable test based on F statistics can be devised to determine when $\chi_{n+1}^2$ is statistically better than $\chi_n^2$ to an appropriate confidence level. The statistic $\chi_{n+1}^2$ is statistically better than the statistic $\chi_n^2$ when $\chi_{n+1}^2$ is less than $\chi_n^2$ by a sufficient amount that, in one test, the probability that the model with n+1 kernels explains the observed intensities less well than the model with n kernels is less than 0.05. In the course of the computational processing of clusters, a partner is added to each of the original kernels and tested, as shown in FIG. 29, to detect potential overlapping fluorophores for each of the original kernels. In alternative embodiments of the present invention, adding and testing of additional partners can be undertaken in additional iterations, in order to detect the unlikely occurrence of three-way and higher-order overlapping fluorophores. In order to more efficiently computationally process the initial kernels in each cluster, partners may be added and tested only for kernels of sufficient, initial amplitude to justify testing the kernels for potential overlap.

Returning to FIG. 24B, in step 2403, the initial spots in a cluster are used to define n initial kernels. In step 2404, these n initial kernels are fit to observe intensities for the area or volume of the cluster. In step 2405, the residual metric $\chi_{current}$ is computed for the initial, best-fit n kernels and the local variable m is set to n. In the inner for-loop of steps 2406-2412, a partner is added to, and tested for, each of the initial kernels. In step 2407, a partner kernel is added to a currently considered kernel for the current iteration of the for-loop of steps 2406-2412. In step 2408, the m+1 kernels including the m kernels prior to the addition of the partner kernel in step 2407 and the partner kernel added in step 2407 are best fit to the observed pixel or voxel intensities within the area or volume of the cluster. In step 2409, a new residual metric $\chi_{m+1}^2$ is computed for the best-fit m+1 kernels. When $\chi_{m+1}^2$ is statistically better than $\chi_C$, as determined in step 2410, then the partner added in step 2407 is accepted as a new kernel, $\chi_C$ is set to $\chi_{m+1}^2$ and m is set to m+1. When there are more kernels of the original kernels to consider in the inner for-loop of steps 2406-2412, as determined in step 2412, control flows back into step 2407 to add a partner to a next kernel of the original kernels. Otherwise, in step 2413, the best-fit m+1 kernels are stored as spots for the cluster. Following consideration of each cluster in the outer for-loop of steps 2402-2414, the spots determined for all clusters are combined into a disambiguated image electronically stored in memory and/or persistent mass storage in step 2416. In alternative embodiments of the present invention, a similar balance between under-fitting and over-fitting additional kernels to clusters can be achieved using the Bayesian information criterion and/or additional techniques.

Figure 30A:
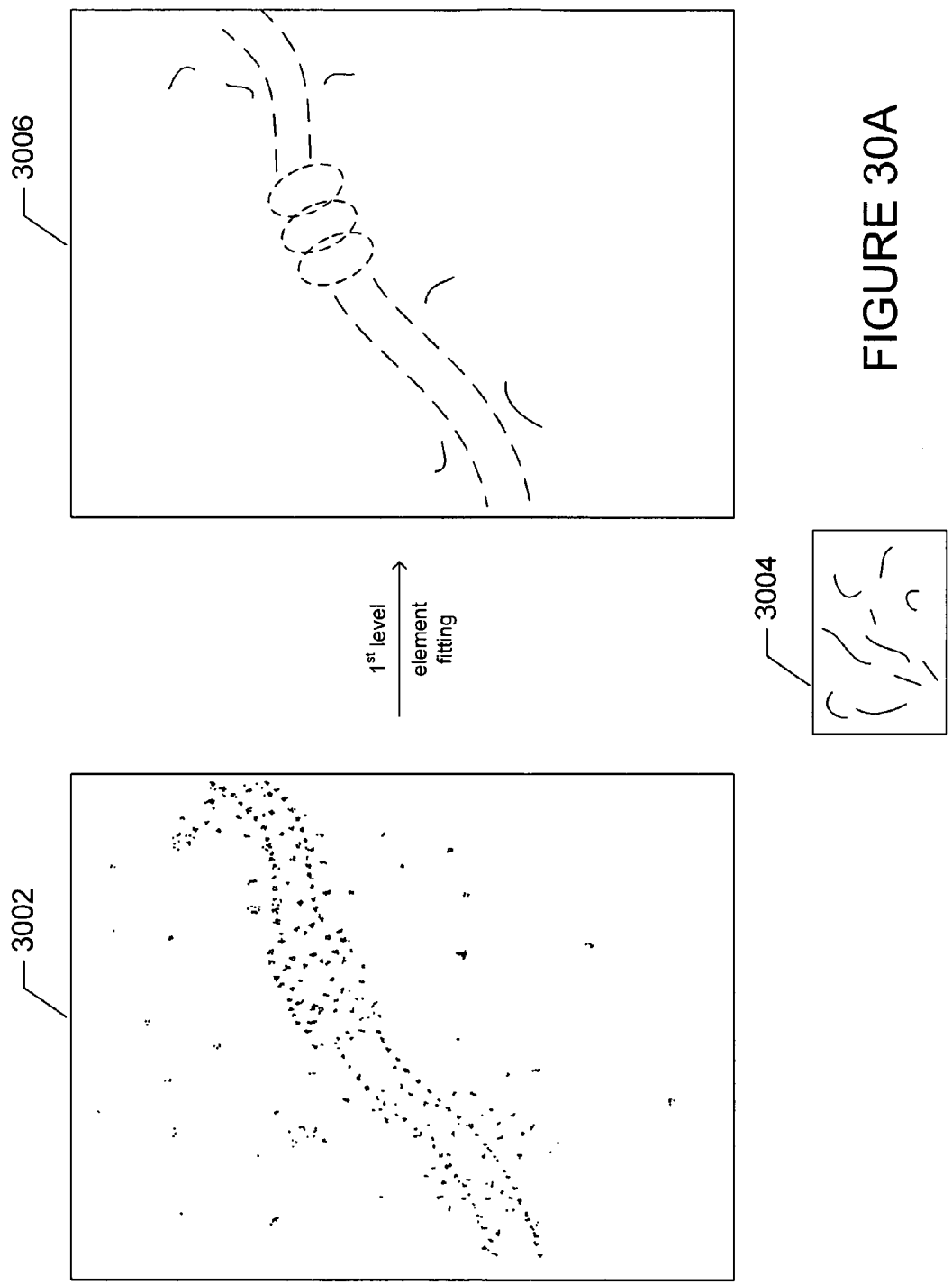
Figure 30C:
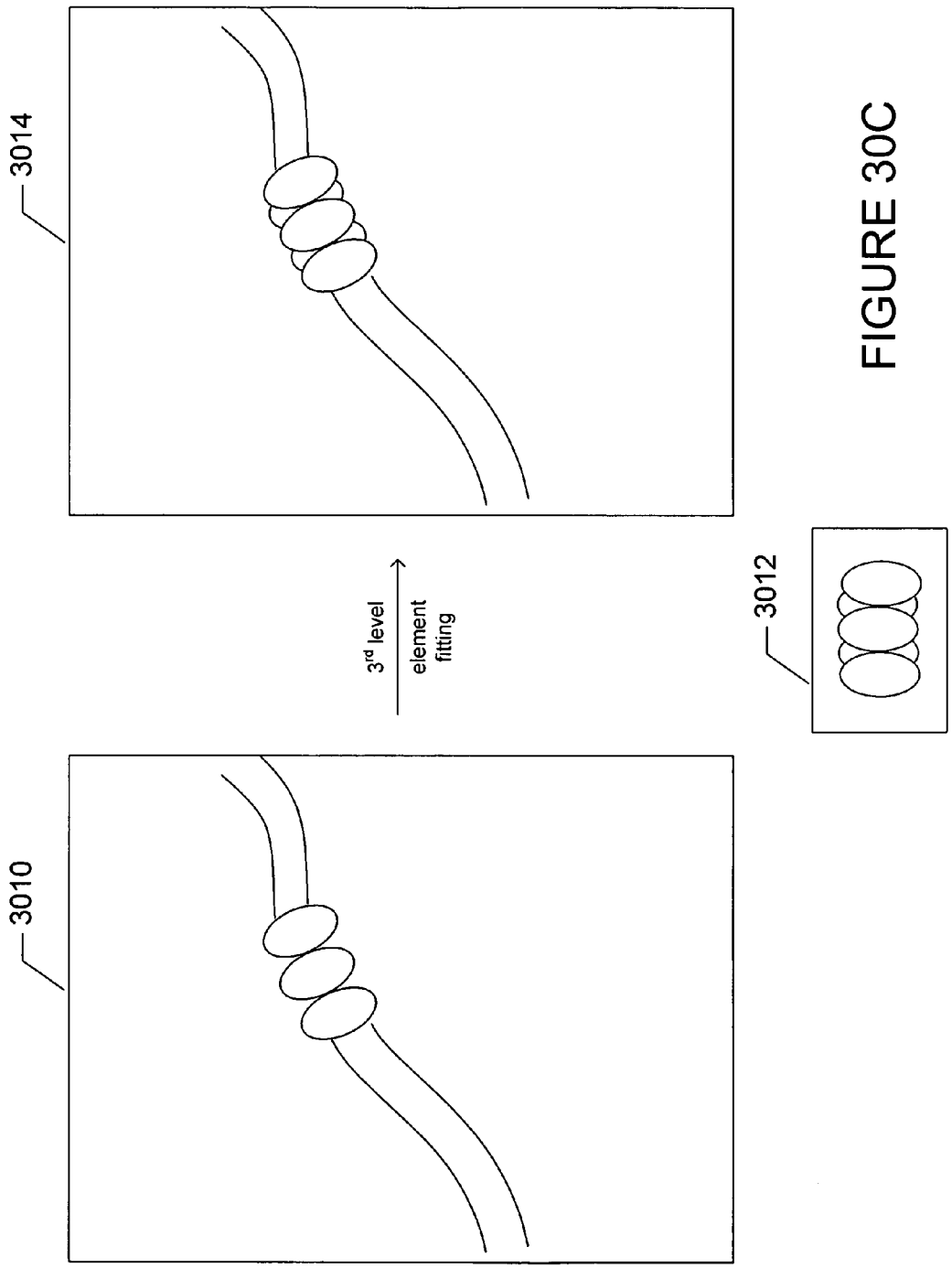

FIGS. 30A-D illustrate the processes carried out in steps 2313 and 2314 of FIG. 23, according to one embodiment of the present invention. In FIG. 30A, the left-hand image 3002 represents a disambiguated, processed image stored in step 2416 of FIG. 24B. This image contains all of the spots, or fluorophore images, initially detected using the spot-metric threshold, in step 2408 of FIG. 24A, as well as additional, obscured, overlapping spots detected in step 2412 of FIG. 24A. The locations and intensities of the spots may have varied with respect to the initial, observed intensities of the spots due to the computational fitting carried out during application of the mixed model, in step 2412 of FIG. 24A. In the iterative, hierarchical, computational-processing step of 2313 in FIG. 23, groups of primitive geometrical elements are matched to groups, or distributions, of spots within the image in order to further refine and interpret the image, and the initially matched primitive geometrical elements are, in subsequent iterations, matched to increasingly complex and/or large geometrical elements. For example, in a first hierarchical level of element fitting, shown in FIG. 30A, a group of primitive geometrical elements 3004 is computationally fit to the spots in the disambiguated image 3002 in order to generate a first, further-refined image 3006. This represents a first level of the hierarchical process of image interpretation that represents one embodiment of the present invention. In a second hierarchical level of element fitting, shown in FIG. 30B, the image produced by the first level of element fitting 3006 is then used as a basis for fitting a second group of geometrical elements 3008 to create a second-level interpreted or refined image 3010. In FIG. 30C, the second-level interpreted or refined image 3010 is further refined and interpreted by fitting elements of a third group of geometrical elements 3012 to the second-level refined or interpreted image 3010 to produce a third-level refined or interpreted image 3014. As illustrated in FIGS. 30A-C, each level of hierarchical element fitting tends to produce a clearer, more highly refined, better-interpreted image in which biological structures are clearly revealed. In general, the geometrical elements at each successive layer of the hierarchical image-processing method are larger, more highly interpreted and meaningful elements that can be constructed from more primitive elements fit to the image in previous levels. Of course, the original disambiguated image 3002 in FIG. 30A remains available throughout the process, to facilitate matching of higher-level elements to lower-level elements, when ambiguities arise.

The hierarchical image-processing method described above, with reference to FIGS. 30A-C, is carried out, in certain embodiments of the present invention, as a recursive state-space search, in which many different sequences of geometrical-element are fitted to the disambiguated-spot image that represents a starting point for the recursive search. The sequence or sequences of geometrical elements that best explain the disambiguated-spot image, or best fits the disambiguated-spot image, are selected as a final, refined image.

Figure 30D:
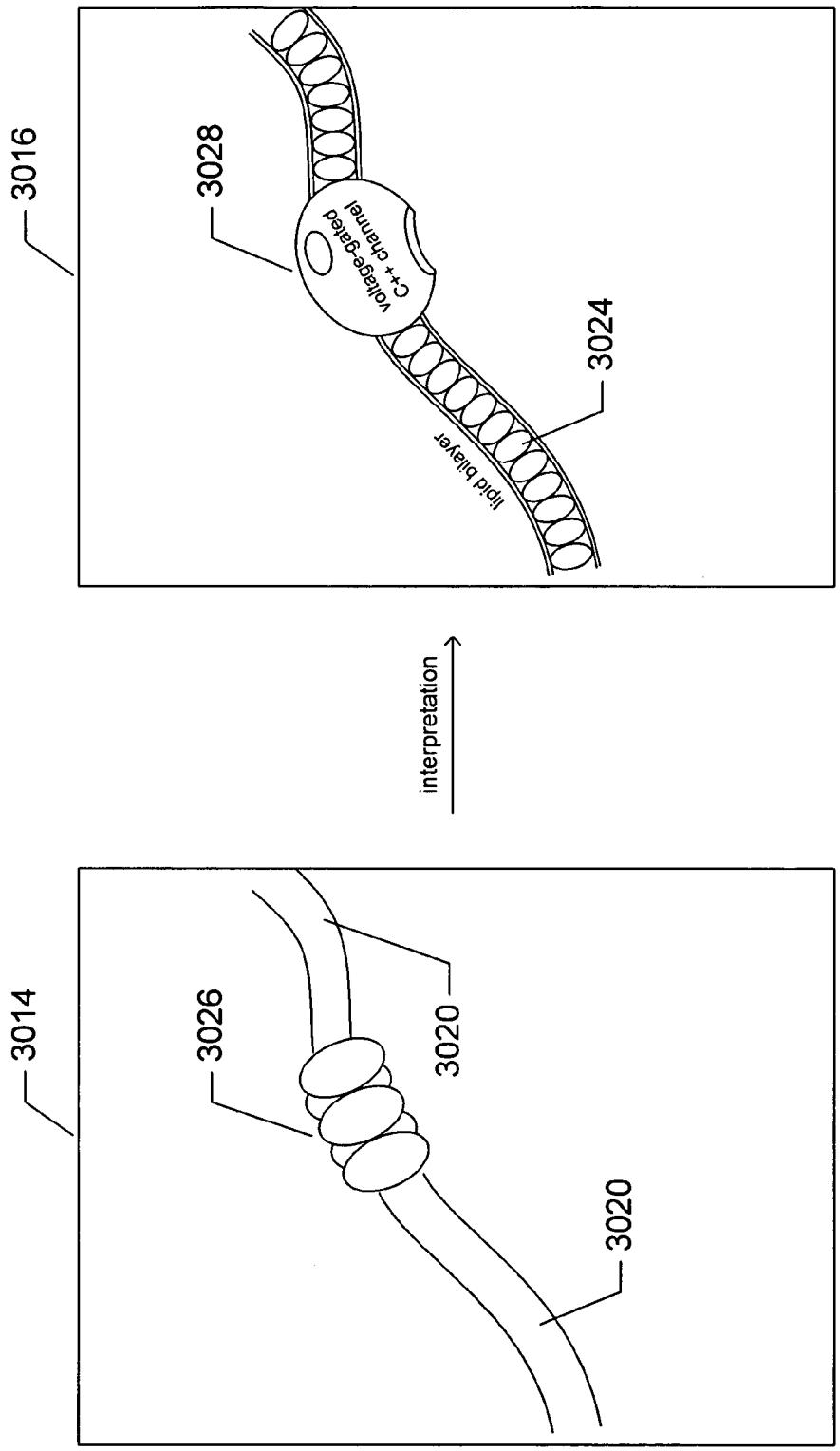

FIG. 30D illustrates step 2314 in FIG. 23. The refined and interpreted image produced by the hierarchical resolution process of step 2313 in FIG. 23 produces refined image 3014. A more interpretive image-processing step can then fit idealized and canonical biological interpretations to the image to produce a final interpretation 3016 corresponding to refined image 3014. For example, in FIG. 30D, the double-layer structure 3020 in the image 3014 is interpreted to be a lipid-bilayer membrane 3024 in the interpretation 3016 and the transmembrane-pore-like structure 3026 is interpreted to be a voltage-gated calcium channel 3028 in the interpreted image 3016.

In both the hierarchical image-resolution process discussed with reference to FIGS. 30A-C and in the final interpretive process discussed with reference to FIG. 30D, additional information about the sample and experimental conditions that produced the sample may be used to facilitate image refinement and interpretation. For example, the geometrical elements fit to spots or lower-level geometrical elements, at each hierarchical level, may be selected from a larger set of geometrical elements based on the type of sample, and fitting of geometrical elements to lower-level elements or disambiguated spots can be constrained by various biological constraints. For example, when a particular type of biopolymer is being imaged, it may be known that the biopolymer has a minimum radius of curvature, as a result of which the biopolymer cannot be looped more tightly than a minimum loop diameter. A matching of curved geometrical elements that would produce a tighter looping than possible may therefore be rejected or disfavored during the geometrical-element fitting process. Such biological constraints may also be applied to reject various intermediate images, produced at each hierarchical level of the hierarchical computational process, after geometrical-element fitting at that level.

Figure 31:
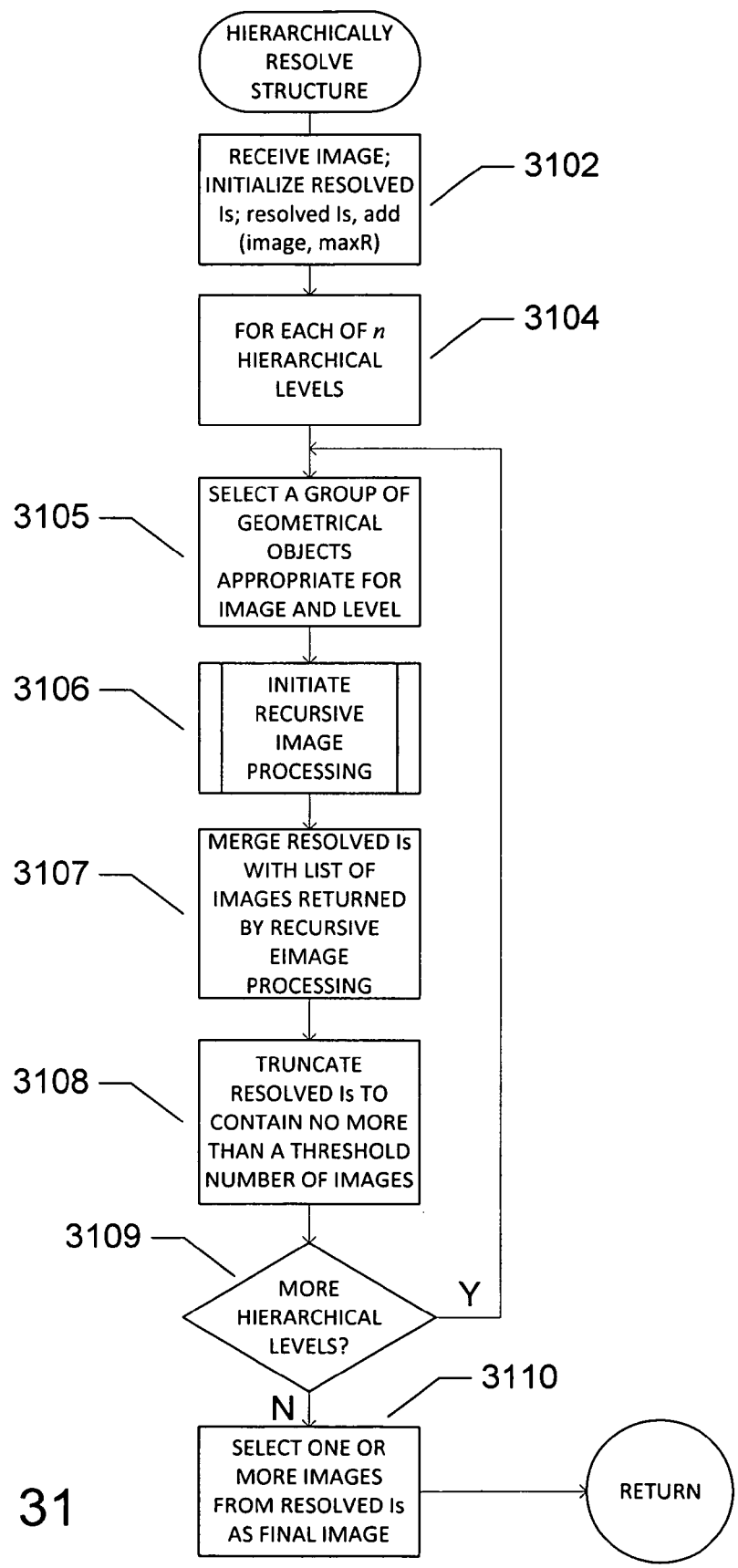
FIGS. 31-33 provide control-flow diagrams that describe the hierarchical computational image processing step 2313 in FIG. 23, according to one embodiment of the present invention.
Figure 32:
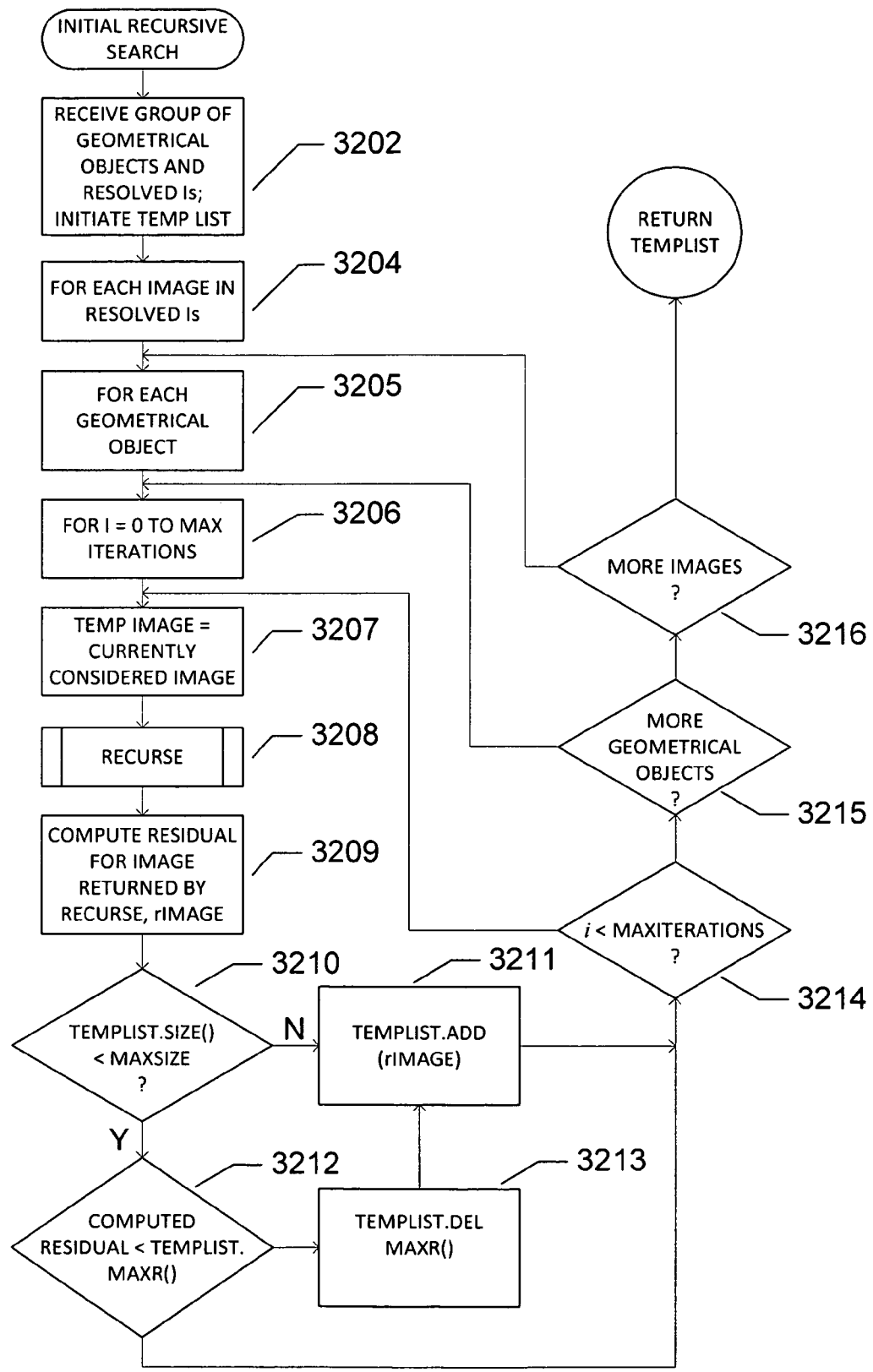
Figure 33:
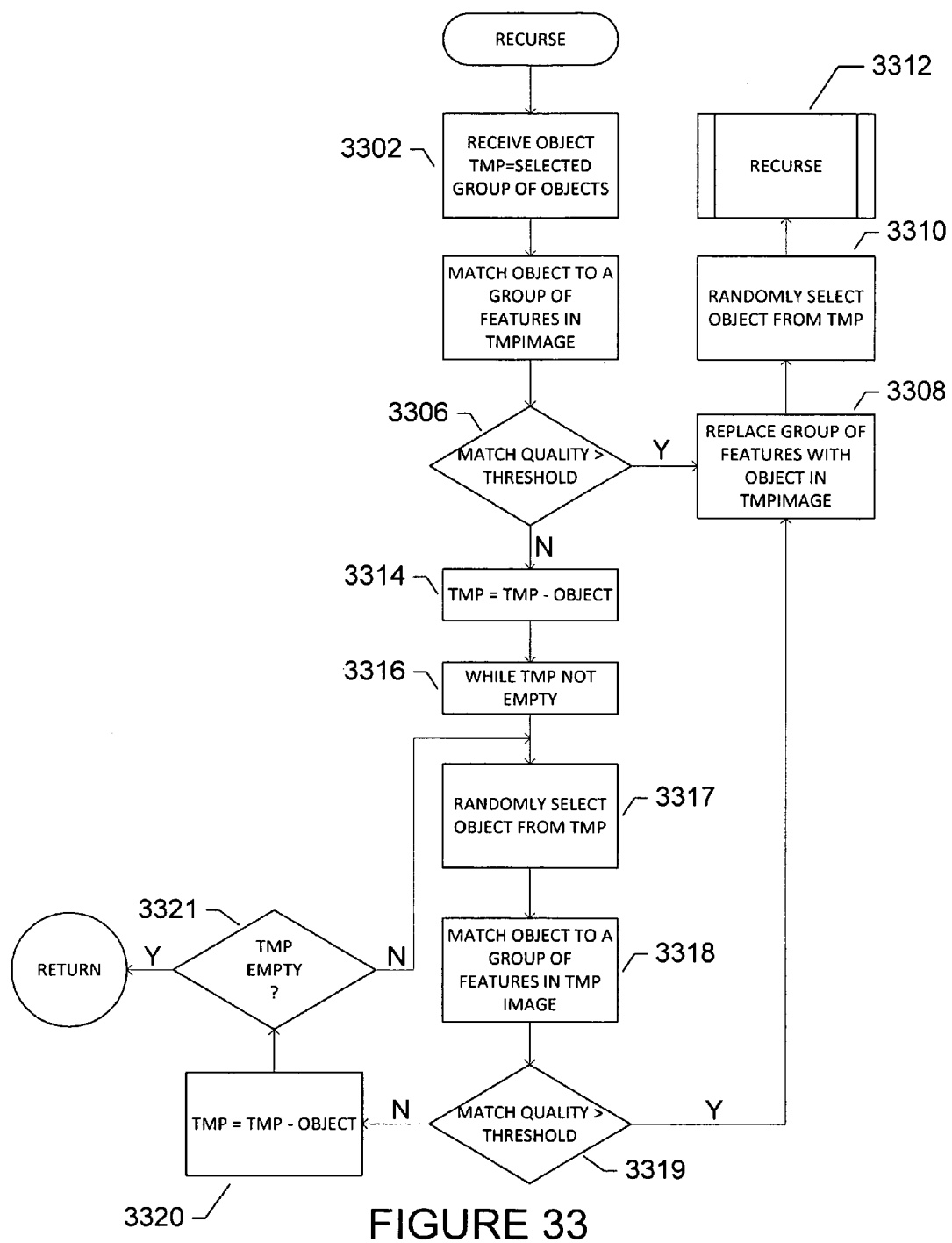

FIGS. 31-33 provide control-flow diagrams that describe the hierarchical computational image processing step 2313 in FIG. 23, according to one embodiment of the present invention. In step 3102, a disambiguated image (3002 in FIG. 30A) is received. A list of images, resolvedIs, is initialized, and the received image is added as the first member to the list of images. In the for-loop of steps 3104-3109, each of the hierarchical levels of processing is carried out. For each hierarchical level, a group of geometrical elements appropriate for the image and level are selected, in step 3105. In step 3106, a recursive procedure is called in order to generate the number of candidate, further-refined images from the images already present in the list of images and selected group of geometrical elements. The list of images returned by the recursive procedure is then merged with the list of images already resident within the list resolvedIs in step 3107. The list resolvedIs is then truncated to contain no more than a threshold number of images. Merging of the list returned by the recursive procedure and the list resolvedIs is carried out by sorting the images with respect to a fitness or residual metric, so that, at each level, only candidate images that best fit the originally received disambiguated image are retained. Finally, in step 3110, one or more of the candidate images in the list resolvedIs are selected as one or more final images.

FIG. 32 provides a control-flow diagram for the recursive procedure called in step 3106 of FIG. 31. In step 3202, a group of geometrical elements and the list resolvedIs are received, and a temporary list of images tempList is initialized. In the for-loop of steps 3204-3216, each of the images currently residing in the list resolvedIs is considered for further resolution and interpretation. In the inner for-loop of steps 3205-3215, a first geometrical element for fitting to the currently considered image is selected from the list of geometrical elements. This represents a starting point for a recursive search for more highly refined and interpreted images obtained by fitting of geometrical elements to the image. In the innermost for-loop of steps 3206-3214, a number maxIterations of recursive searches is carried out for each geometrical-element starting point currently considered in the for-loop of steps 3205-3215. The recursive search is called in step 3208 and, in step 3209, a residual or fitness metric with respect to the originally received, disambiguated image is computed for the refined image returned by the call to the routine "recurse." When the number of images in tempList is less than some maximum size, as determined in step 3210, the image returned by the call to the routine "recurse" is added to the list tempList in step 3211. Otherwise, when the computed residual metric is less than the smallest computed metric of any image in the list tempList, as determined in step 3212, the image with the largest residual metric in tempList is deleted, in step 3213, and the image returned by the call to recurse is added to the list tempList, in step 3211. In step 3214, the routine determines whether or not to continue the innermost for-loop. In step 3215, the routine determines whether or not to consider the middle-level for-loop of steps 3205-3215. In step 3216, the routine determiners whether or not there are more images to consider in the outermost for-loop of steps 3204-3216.

FIG. 33 provides a control-flow diagram for the routine "recurse," called in step 3208 of FIG. 32. In step 3302, the geometrical-element starting point is received, and the local variable tmp is set to the group of geometrical elements selected for the current hierarchical processing level, in step 3105 of FIG. 31. In step 3304, the received element is matched to a group of features in the received image. The matching step 3304 seeks a matching of the element to one or more lower-level elements or spots of the image that produces a match-quality value greater than a threshold value. When the quality of the match is greater than the threshold value, as determined in step 3306, the group of features to which the element is matched is replaced with the element, in step 3308, another element is randomly selected from the group of elements tmp in step 3310, and the routine "recurse" is recursively called in step 3312. Otherwise, the element is removed from the group of elements tmp in step 3314. Then, in the while-loop of steps 3316-3321, an element is randomly selected from the group of elements tmp, in step 3317, and that element is matched to a group of features in the image in step 3318. When the match quality is greater than some threshold quality, as determined in step 3319, then the group of features is replaced with the element, in step 3308, an element is randomly selected from tmp, in step 3310, and the routine "recurse" is recursively called in step 3312. Otherwise, the element is removed from the list of elements tmp, in step 3320. When the list of elements tmp is not empty, as determined in step 3321, then the while-loop of steps 3316-3321 is re-entered, for a next iteration. Otherwise, the routine "recurse" returns.

The match-quality metric used in steps 3306 and 3319 may include a variety of different considerations in various embodiments of the present invention. The match quality may be computed to reflect how well the geometrical element covers or overlaps the group of features in the image that it is being fit to. Match quality may also incorporate various external information about the sample from which the image is obtained, to forestall matches that would produce improbable or impossible higher-level features. In the matching steps of 3304 and 3318, elements may be rotated and/or scaled, in two dimensions or three dimensions, depending on the dimensionality of the image-processing task, in order to achieve best fits to lower-level features, although both scaling and rotation may be constrained by external information.

Figure 34:
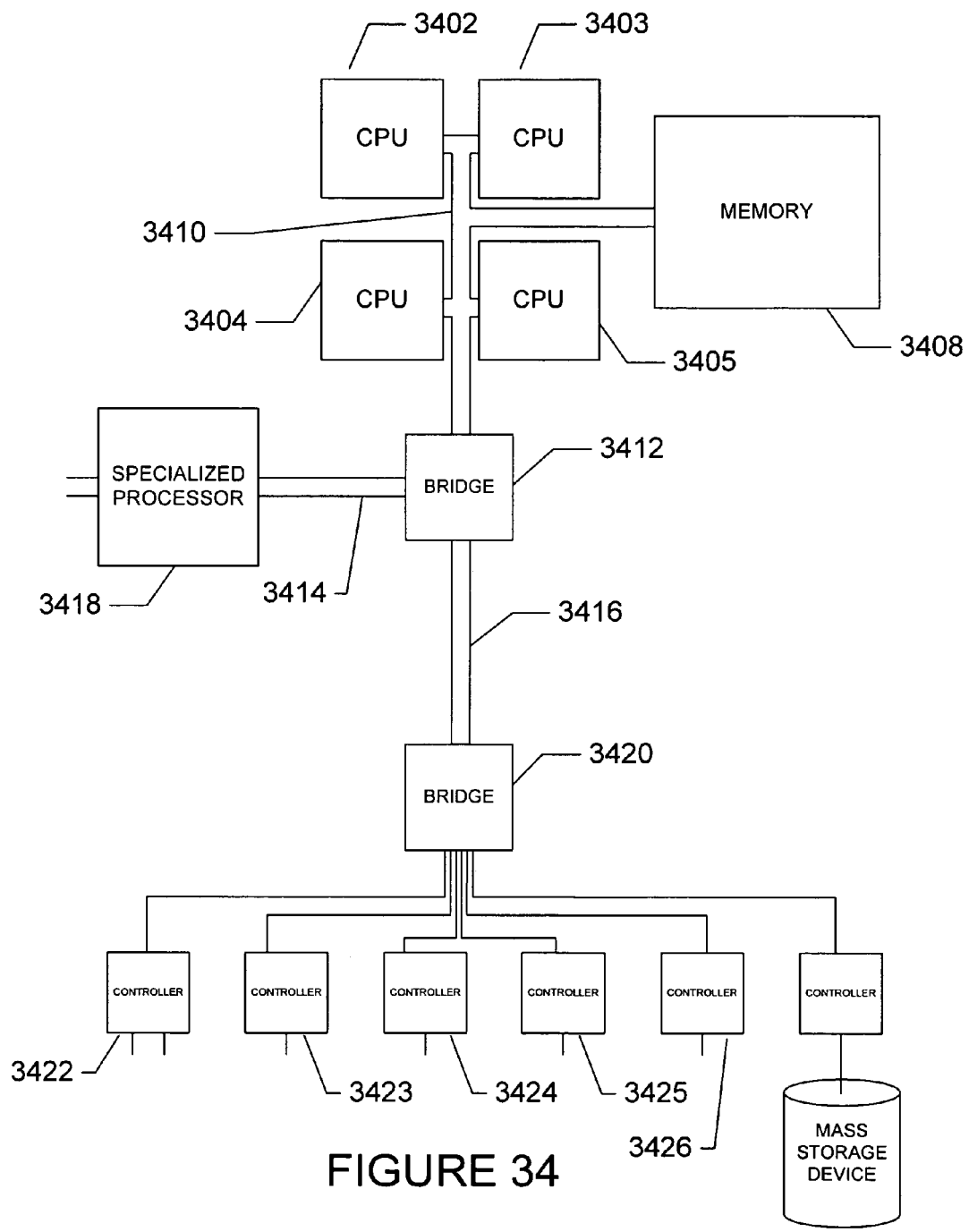
FIG. 34 illustrates a typical electronic computer that executes the image-processing steps within an imaging system that represents one embodiment of the present invention.

FIG. 34 illustrates a typical electronic computer that executes the image-processing steps within an imaging system that represents one embodiment of the present invention. The computer system contains one or multiple central processing units ("CPUs") 3402-3405, one or more electronic memories 3408 interconnected with the CPUs by a CPU/memory-subsystem bus 3410 or multiple busses, a first bridge 3412 that interconnects the CPU/memory-subsystem bus 3410 with additional busses 3414 and 3416, or other types of high-speed interconnection media, including multiple, high-speed serial interconnects. These busses or serial interconnections, in turn, connect the CPUs and memory with specialized processors, such as a graphics processor 3418, and with one or more additional bridges 3420, which are interconnected with high-speed serial links or with multiple controllers 3422-3427, such as controller 3427, that provide access to various different types of mass-storage devices 3428, electronic displays, input devices, and other such components, subcomponents, and computational resources. Embodiments of the present invention may also be implemented on distributed computer systems and can also be implemented partially in hardware logic circuitry.

Although the present invention has been described in terms of particular embodiments, it is not intended that the invention be limited to these embodiments. Modifications will be apparent to those skilled in the art. For example, many different implementations of the computational-processing methods used in imaging systems that represent embodiments of the present invention can be obtained by varying common implementation parameters, including programming language, control structures, modular organization, data structures, underlying operating system, and other implementation parameters. These computational image-processing steps are incorporated within a fluorescence-microscopy instrument or other imaging system that includes both optical components and detectors, such as those discussed above with reference to FIG. 7, as well as data-processing and data-storage components, often including high-capacity, multi-processor computer systems and high-capacity electronic memories and mass-storage devices. While the described embodiments of the present invention are directed to fluorescence microscopy, alternative embodiments of the present invention may be directed to other types of microscopy, optical imaging, or other types of imaging in which multiple, intermediate images are acquired and combined to generate final images.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. An imaging system comprising:
a light-detection subsystem that illuminates a sample or a portion of the sample to activate light emitters within the sample, excites light emission from the light emitters, and records, over a period of time, intermediate output images of light emitters within the sample or the portion of the sample;
an image-generation subsystem that processes the intermediate output images to identify and record initially determined positions of the light emitters within the sample or the portion of the sample and that iteratively computes computed output images from light-emitter-position models in order to disambiguate overlapping light-emitter images in the intermediate output images to produce a composite image that includes indications of the positions of the light emitters within the sample or the portion of the sample; and
an image-interpretation subsystem that iteratively fits geometric primitives to the composite image, produced by the image-generation subsystem, in order to produce one or more refined and interpreted images of the sample or the portion of the sample.

2. The imaging system of claim 1 wherein the light-detection subsystem comprises a fluorescence-microscopy optical subsystem.

3. The imaging system of claim 2 wherein the light emitters are fluorophores which are activated by illumination by exposure to light of a first frequency and which are excited to emit fluorescent light by exposure to light of a second frequency.

4. The imaging system of claim 3 wherein the light emitters are fluorophores which are activated exposure to light of a first frequency and which are excited to emit fluorescent light by exposure to light of a second frequency.

5. The imaging system of claim 1 wherein the image-generation subsystem processes each intermediate image by:
filtering noise from the intermediate image to produce a noise-filtered intermediate image;
selecting local maxima from the noise-filtered intermediate image;
selecting light emitters from the selected local maxima; and
disambiguating overlapping light-emitter images in order to add any additional, detected light emitters to the selected light-emitter positions.

6. The imaging system of claim 5 wherein the image-generation subsystem filters noise from the intermediate image by applying a Gaussian filter to the intermediate images.

7. The imaging system of claim 5 wherein the image-generation subsystem selects local maxima from the noise-filtered intermediate image by selecting pixels or voxels that have higher associated intensity values than all adjacent pixels or voxels in the intermediate image.

8. The imaging system of claim 5 wherein the image-generation subsystem selects light emitters from the selected local maxima by:
computing a spot metric for each local maximum as the product of a curvature computed over a neighborhood of the local maximum in the image and the mean intensity of a neighborhood of the local maximum; and
selecting, as light emitters, those local maxima with computed spot metrics greater than a threshold value.

9. The imaging system of claim 5 wherein the image-generation subsystem disambiguates overlapping light-emitter images in order to add any additional, detected light emitters to the selected light emitters by:
partitioning the light emitters into clusters that each comprises one or more initial light emitters; and
for each cluster,
iteratively
inserting a partner to a selected initial light emitter into the cluster,
fitting initial light-emitter positions and the partner position to observed intensities for the cluster,
computing a computed image for the cluster,
computing a residual statistic from the computed image and observed image, and
adding the partner to the cluster when a statistical test indicates that the residual statistic computed for the cluster including the partner is better than the residual statistic computed for the cluster prior to inserting the partner.

10. The imaging system of claim 9 wherein computing a computed image for the cluster further includes modeling each light-emitter and the partner as parameterized Gaussian intensity distributions.

11. The imaging system of claim 1 wherein each intermediate image comprises a number of two-dimensional images obtained over a range of sample position relative to the optical axis of the imaging system.

12. The imaging system of claim 1 wherein the image-interpretation subsystem iteratively fits geometric primitives to the composite image, produced by the image-generation subsystem, in order to produce one or more refined and interpreted images of the sample or the portion of the sample by:
iteratively
selecting a set of geometrical elements for a currently considered hierarchical processing level;
recursively fitting geometrical elements from the set of geometrical elements to an intermediate, refined image from a preceding iteration or, in a first iteration, to the composite image produced by the image-generation subsystem to produce one or more candidate refined images; and
selecting candidate refined images for processing in a subsequent iteration or, in a final iteration, as the one or more refined and interpreted images.

13. The imaging system of claim 12 wherein the image-interpretation subsystem selects a set of geometrical elements for a currently considered hierarchical processing level by:
selecting geometrical elements with sizes and complexities appropriate to the currently considered hierarchical processing level; and
selecting, from among those geometrical elements with sizes and complexities appropriate to the currently considered hierarchical processing level, geometrical elements compatible with structures and features known to occur within the sample.

14. The imaging system of claim 12 wherein the image-interpretation subsystem carries out a geometrical-element-fitting search in order to consider a large number of possible mappings of geometrical elements to the intermediate, refined image from a preceding iteration or, in the first iteration, to the composite image produced by the image-generation subsystem.

15. The imaging system of claim 14 wherein candidate images are evaluated by the extent to which features of the intermediate, refined image from a preceding iteration or, in the first iteration, of the composite image produced by the image-generation subsystem, are covered, or contained within, the geometrical elements fitted to them in the current iteration as well as by the likelihood that features in the candidate images correspond to structures and features known to occur in the sample.

16. The imaging system of claim 14 wherein a fit of a geometrical element to one or more features of the intermediate, refined image from a preceding iteration or, in the first iteration, to the composite image produced by the image-generation subsystem, is evaluated by the extent to which features of the intermediate, refined image from a preceding iteration or, in the first iteration, of the composite image produced by the image-generation subsystem, are covered, or contained within, the geometrical element as well as by the likelihood that any intermediate feature in the candidate image produced by fitting the geometrical element to the one or more features corresponds to structures and features known to occur in the sample.

17. A method for producing an image, the method comprising:
    repeatedly
        illuminating a sample or a portion of the sample to activate light emitters within the sample,
        exciting light emission from the light emitters, and
        recording, over a period of time, intermediate output images of light emitters within the sample or the portion of the sample;
    processing the intermediate output images to identify and record initially determined positions of the light emitters within the sample or the portion of the sample;
    iteratively computing computed output images from light-emitter-position models in order to disambiguate overlapping light-emitter images in the intermediate output images to produce a composite image that includes indications of the positions of the light emitters within the sample or the portion of the sample; and
    iteratively fitting geometric primitives to the composite image, produced by the image-generation subsystem, in order to produce one or more refined and interpreted images of the sample or the portion of the sample.

18. The method of claim 17 wherein processing the intermediate output images to identify and record initially determined positions of the light emitters within the sample or the portion of the sample further includes:
    filtering noise from the intermediate image to produce a noise-filtered intermediate image;
    selecting local maxima from the noise-filtered intermediate image;
    selecting light emitters from the selected local maxima; and
    disambiguating overlapping light-emitter images in order to add any additional, detected light emitters to the selected light-emitter positions.

19. The method of claim 17 wherein iteratively computing computed output images from light-emitter-position models in order to disambiguate overlapping light-emitter images in the intermediate output images to produce a composite image that includes indications of the positions of the light emitters within the sample or the portion of the sample further includes:
    partitioning the light emitters into clusters that each comprises one or more initial light emitters; and
    for each cluster,
        iteratively
            inserting a partner to a selected initial light emitter into the cluster,
            fitting initial light-emitter positions and the partner position to observed intensities for the cluster,
            computing a computed image for the cluster,
            computing a residual statistic from the computed image and observed image, and
            adding the partner to the cluster when a statistical test indicates that the residual statistic computed for the cluster including the partner is better than the residual statistic computed for the cluster prior to inserting the partner.

20. The method of claim 17 wherein iteratively fitting geometric primitives to the composite image, produced by the image-generation subsystem, in order to produce one or more refined and interpreted images of the sample or the portion of the sample further includes:
    iteratively
        selecting a set of geometrical elements for a currently considered hierarchical processing level;
        recursively fitting geometrical elements from the set of geometrical elements to an intermediate, refined image from a preceding iteration or, in a first iteration, to the composite image produced by the image-generation subsystem to produce one or more candidate refined images; and
        selecting candidate refined images for processing in a subsequent iteration or, in a final iteration, as the one or more refined and interpreted images.

* * * * *